US009320815B2

(12) United States Patent
Kassis

(10) Patent No.: US 9,320,815 B2
(45) Date of Patent: Apr. 26, 2016

(54) COMPOUNDS AND METHODS FOR ENZYME-MEDIATED TUMOR IMAGING AND THERAPY

(71) Applicant: President and Fellows of Harvard College, Cambridge, MA (US)

(72) Inventor: Amin I. Kassis, Chestnut Hill, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 101 days.

(21) Appl. No.: 13/792,966

(22) Filed: Mar. 11, 2013

(65) Prior Publication Data

US 2013/0336887 A1 Dec. 19, 2013

Related U.S. Application Data

(63) Continuation of application No. 12/476,102, filed on Jun. 1, 2009, now Pat. No. 8,394,953, which is a continuation of application No. PCT/US2007/024659, filed on Nov. 30, 2007.

(60) Provisional application No. 60/872,073, filed on Dec. 1, 2006, provisional application No. 60/912,688, filed on Apr. 19, 2007, provisional application No. 60/949,240, filed on Jul. 11, 2007.

(51) Int. Cl.
*A61K 51/04* (2006.01)
*C07D 239/74* (2006.01)
*C07D 239/86* (2006.01)
*C07D 239/91* (2006.01)
*C07D 239/94* (2006.01)

(52) U.S. Cl.
CPC .......... *A61K 51/0459* (2013.01); *C07D 239/74* (2013.01); *C07D 239/86* (2013.01); *C07D 239/91* (2013.01); *C07D 239/94* (2013.01)

(58) Field of Classification Search
CPC .. C07D 239/74; C07D 239/86; C07D 239/91; C07D 239/94; A61K 51/0459
See application file for complete search history.

(56) References Cited

U.S. PATENT DOCUMENTS

| | | | |
|---|---|---|---|
| 3,526,627 A | 9/1970 | Brooks, Jr. | |
| 3,772,274 A | 11/1973 | Kaplan | |
| 5,316,906 A | 5/1994 | Haugland et al. | |
| 7,514,067 B2 | 4/2009 | Kassis et al. | |
| 8,394,953 B2 | 3/2013 | Kassis | |
| 2003/0021791 A1 | 1/2003 | Kassis et al. | |
| 2003/0049689 A1 | 3/2003 | Edwards et al. | |
| 2003/0199526 A1 | 10/2003 | Choquette | |
| 2004/0265228 A1 | 12/2004 | Levitzki et al. | |
| 2006/0217377 A1* | 9/2006 | Gonzalez, III | C07D 413/12 514/234.2 |
| 2009/0285755 A1 | 11/2009 | Kassis et al. | |

FOREIGN PATENT DOCUMENTS

| | | | |
|---|---|---|---|
| WO | WO 03016292 A1 * | 2/2003 | |
| WO | WO-2004/078733 | 9/2004 | |
| WO | WO2004078733 A1 * | 9/2004 | |
| WO | WO-2006/028904 | 3/2006 | |
| WO | WO-2006/066044 | 6/2006 | |
| WO | WO 2006/105081 | 10/2006 | |
| WO | WO 2007125331 A2 * | 11/2007 | |

OTHER PUBLICATIONS

Ding et. al., "18F-Labeled Tracers for Positron Emission Tomography Studies in the Neurosciences", ACS Symposium Series, Biomedical Frontiers of Fluorine Chemistry, 1996, American Chemical Society, vol. 639, pp. 328-343.*

Davis et al., Hydrogeology Journal, 1998, Springer-Verlag, vol. 6, pp. 104-114.

Frohman et al., "Dipeptidylpeptidase IV and trypsin-like enzymatic degration of human growth hormone-releasing hormone in plasma", J. Clin. Invest., vol. 83, pp. 1533-1540 (1989).

Belaaouaj et al, "Matrix metalloproteinases cleave tissue factor pathway inhibitor: Effects on coagulation", The Journal of Biological Chemistry, vol. 275, No. 35, pp. 27123-27128 (2000).

The International Search Report and Written Opinion dated Apr. 22, 2008 for corresponding PCT application No. PCT/US07/24659.

Roy et al., "Auto-Redox Reaction: Tin(II) Chloride-Mediated One-Step Reductive Cyclization Leading to the Synthesis of Novel Biheterocyclic 5,6-Dihydro-quinazolino[4,3-b]quinazoline-8-ones with Three-Point Diversity", Journal of Organic Chemistry, vol. 71, pp. 382-385 (2006).

Hayakawa et al., "Synthesis and biological evaluation of 4-morpholino-2-phenylquinazolines and related derivatives as novel PI3 kinase p110a inhibitors", Bioorganic and Medicinal Chemistry, vol. 14, pp. 6847-6858 (2006).

Tachikawa et al., "Studies on 1,3-Benzoxazines. VI. Formation of Quinazolines and 4H-3,1-Benzoxazines by the Reaction of 4-Chloro-2H-1,3-benzoxazines with Aminoacetophenone, Aminobenzophenone and Aminobenzyl Alcohol Derivatives", Chemical and Pharmaceutical Bulletin, vol. 30, No. 2, pp. 559-563 (1982).

Ho et al., "Synthesis and Biologic Evaluation of a Radioiodinated Quinazolinone Derivative for Enzyme-Mediated Insolubilization Therapy", Bioconjugate Chemistry, vol. 13, pp. 357-364 (2002).

Chen et al., "Molecular-Docking-Guided Design, Synthesis, and Biologic Evaluation of Radioiodinated Quinazolinone Prodrugs", Journal of Medicinal Chemistry, vol. 50, pp. 663-673 (2007).

Layeva et al., "Synthesis of 5- and 7-fluoroquinazolin-4(1H)-ones", Russian Chemical Bulletin, International Edition, vol. 56, No. 9, pp. 1821-1827 (2007).

(Continued)

*Primary Examiner* — Sarah Pihonak
(74) *Attorney, Agent, or Firm* — McDonnell Boehnen Hulbert & Berghoff LLP

(57) ABSTRACT

The invention provides methods and compositions, e.g., for tumor imaging and therapy.

4 Claims, 25 Drawing Sheets

(56) References Cited

OTHER PUBLICATIONS

Wang et al., "Radiotracer-based method for determining water solubility of highly insoluble compounds", Journal of Labelled Compounds and Radiopharmaceuticals, vol. 49, pp. 773-788 (2006).

Hour et al., "Synthesis and Cytotoxicity of 6-Pyrrolidinyl-2(2-substituted phenyl)-4-quinazolinones", Journal of the Chinese Chemical Society, vol. 54, pp. 785-790 (2007).

Wang et al., "DMSO increases radioiodination yield of radiopharmaceuticals", Applied Radiation and Isotopes, vol. 66, pp. 50-59 (2008).

Chen et al., "In silico design, synthesis and biological evaluation of radioiodinated quinazolinone derivatives for alkaline phosphatase-mediated cancer diagnosis and therapy", Molecular Cancer Therapeutics, vol. 5, pp. 3001-3013 (2006).

Pospisil et al., "Computational Modeling and Experimental Evaluation of a Novel Prodrug for Targeting the Extracellular Space of Prostate Tumors", Cancer Research, vol. 67, No. 5, pp. 2197-2205 (2007).

Supplemental European Search Report dated Apr. 28, 2011 in corresponding European Patent Application No. 07853203.3.

* cited by examiner

Quinazolinone derivative – Q$_{NH}$ – post enzymatic hydrolysis

Fluoroquinazolinone – ¹⁸FQ$_{NH}$
Prodrug for Imaging (PET) of ALP Expressing Tumors
(e.g. ovarian cancer)

Astatoquinazolinone – $^{211}AtQ_{NH}$
Prodrug for Therapy of GB Expressing Tumors
(e.g. breast cancer)

Iodoquinazolinone – $^{123}IQ_{NH}$
Prodrug for Imaging (SPECT) of PSA and/or PAP Expressing Tumors
(e.g. prostate cancer)

Iodoquinazolinone – $^{123}IQ_{NH}$
Prodrug for Therapy of MMP and/or ALP Expressing Tumors
(e.g. ovarian cancer)

Iodoquinazolinone – ¹³¹IQ_NH
Prodrug for Therapy of GB and/or ALP Expressing Tumors (e.g. lung cancer)

Astatoquinazolinone – ²¹¹AtQ_NH
Prodrug for Therapy of Pep, GB, and/or ALP Expressing Tumors
(e.g. breast cancer)

Quinazoline derivative – $Q_{NN}$ – post enzymatic hydrolysis

Astatoquinazoline – ²¹¹AtQ_NN
Prodrug for Therapy of GB Expressing Tumors
(e.g. lung cancer)

Iodoquinazoline – $^{131}IQ_{NN}$
Prodrug for Therapy of PSMA, GB, and/or PAP Expressing Tumors
(e.g. prostate cancer)

Bismuth-DTPA-Quinazoline – $^{213}$BiQ$_{NN}$
Prodrug for Therapy of GB, MMP, ALP, and/or HS-1 Expressing Tumors
(e.g. colon cancer)

Quinazoline derivative – $Q_{NN}$ – post enzymatic hydrolysis

Technetium-DADT-quinazoline – $^{99m}$TcQ$_{NN}$
Prodrug for Imaging of GB and/or PAP Expressing Tumors
(e.g. prostate cancer)

Technetium-DADT-Di-Quinazoline – $^{99m}$Tc(Q$_{NN}$)$_2$
Prodrug for Imaging of PAP Expressing Tumors (e.g. prostate cancer)

Iodoquinazolinone – $^{131}$IQNH
Prodrug for Therapy of GB and ALP Expressing Tumors
(e.g. lung cancer)

Iodoquinazolinone – ¹²⁴IQNH
Prodrug for imaging (PET) of HS-1 Expressing Tumors
(e.g. pancreatic cancer)

Fluoroquinazoline – $^{18}$FQNN
Prodrug for Imaging (PET) of PSMA Expressing Tumors (e.g. prostate cancer)

Iodoquinazoline – ¹³¹IQNN
Prodrug for Therapy of ALP Expressing Tumors
(e.g. ovarian cancer)

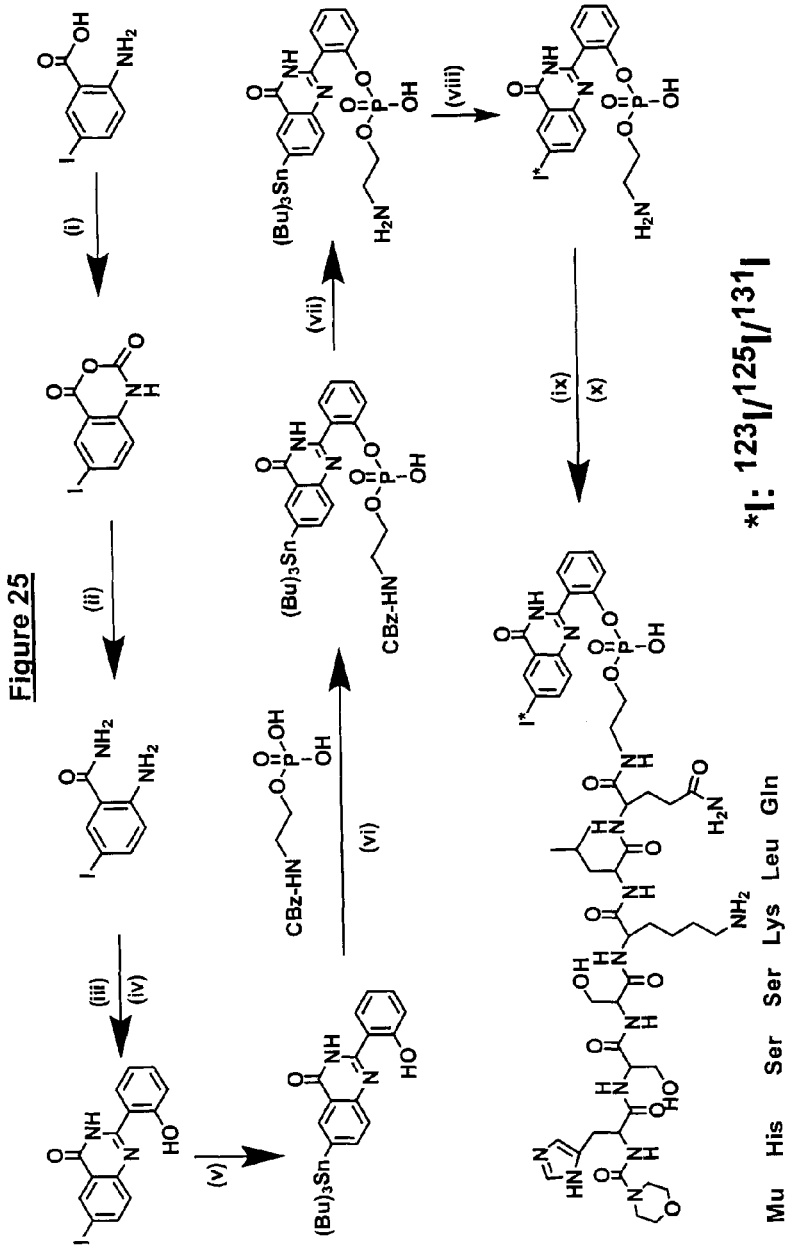

Figure 25

Reagents and conditions: (i) Triphosgene/THF; (ii) 28% Aqueous ammonium hydroxide/THF, DIC/DMF; (iii) Salicylaldehyde, p-toluene sulfonic acid; (iv) 2,3-Dichloro-5,6-dicyano-1,4-benzoquinone; (v) [(Bu)$_3$Sn]$_2$/dioxane; (vi) dicyclohexylcarbodiimide, dimethylaminopyridine; (vii) palladium/charcoal, hydrogenolysis; (viii) Na*I/Iodogen; (xi) dicyclohexylcarbodiimide, 1-hydroxybenzotriazole; (x) 20% piperidine in dimethylformamide;

*I: $^{123}$I/$^{125}$I/$^{131}$I

COMPOUNDS AND METHODS FOR ENZYME-MEDIATED TUMOR IMAGING AND THERAPY

CROSS-REFERENCE TO RELATED APPLICATIONS

This application is a continuation of U.S. patent application Ser. No. 12/476,102, filed Jun. 1, 2009, allowed, which is a continuation of PCT Patent Application No. PCT/US2007/024659, filed Nov. 30, 2007 (which was filed in English and designated the U.S.), which claims the benefit of U.S. Provisional Patent Application No. 60/872,073, filed Dec. 1, 2006; U.S. Provisional Patent Application No. 60/912,688, filed Apr. 19, 2007; and U.S. Provisional Patent Application No. 60/949,240, filed Jul. 11, 2007. The contents of each of these applications are incorporated herein by reference.

GOVERNMENT SUPPORT

This invention was made at least in part with funding from the U.S. Department of Defense, Grant Nos. W81XWH-04-1-0499, W81XWH-06-1-0043, and 000 W81XWH-06-1-0204. The U.S. Government has certain rights in the invention.

BACKGROUND OF THE INVENTION

Radiolabeled diagnostic and therapeutic agents are used for the diagnosis and treatment of cancer and related conditions. To be effective, a diagnostic or therapeutic agent should be capable of localization at the site of interest, e.g., at a tumor site, in order to provide sufficient specificity.

Ideally, radiolabeled agents for cancer imaging and therapy should meet as many of the following criteria as possible: (i) be stable in blood following their administration in a subject; (ii) be taken up rapidly by tumors ($T_{1/2}$ in circulation shorter than the decay half-life of the radionuclide); (iii) be retained for long periods of time within tumors ($T_{1/2}$ in tumors shorter than the decay half-life of the radionuclide); (iv) be concentrated efficiently by tumors (i.e. high % ID/g); (v) be taken up minimally by normal tissue cells; (vi) have a short residence in normal tissues (i.e., short effective half-life in blood, bone marrow, and whole body); (vii) achieve high tumor-to-normal-tissue uptake ratios; and (viii) be labeled with an emitter whose decay characteristics are suitable for imaging (PET or SPECT) or radiotherapy. Additional desirable characteristics of a therapeutic agent include: (i) be labeled with an energetic particle emitter, (ii) attain an intratumoral distribution that is sufficiently uniform to match the range of the emitted particles (i.e. all tumor cells are within the range of the emitted particles), and (iii) achieve an intratumoral concentration that is sufficiently high to deposit a tumorcidal dose in every cell that is within the range of the emitted particle. Conventional reagents generally do not meet all these requirements, and, as a result, are ineffective for therapy or may cause side effects when administered to a subject.

One approach to this problem is known as Enzyme-Mediated Cancer Imaging and Therapy (EMCIT). In EMCIT, a water-soluble, radiolabeled prodrug is administered to the subject; when the prodrug reaches the tumor site, it is hydrolyzed to a water-insoluble form by an enzyme which is present within solid tumors at higher concentrations that those present in normal tissues (see, e.g., Ho et al., *Bioconj. Chem.* 13:357 (2002). The water-insoluble radiolabeled compound then precipitates in the extracellular space around the tumor cells, where its insolubility prevents further biodistribution. When the trapped compound is radiolabeled with a gamma or positron emitting radionuclide, it will enable the selective imaging (SPECT/PET) of tumors. On the other hand, when the trapped molecule is radiolabeled with an energetic alpha- or beta-particle-emitting radionuclide, it will irradiate the tumor mass and eradicate the tumor. See, e.g., U.S. Patent Application Publication 2003-0021791. However, while this approach can provide greater site specificity than conventional methods, improved properties of the water-soluble prodrug and the water-insoluble form would be desirable.

SUMMARY OF THE INVENTION

The present invention relates generally to a novel technology that aims to concentrate RadioActive Prodrugs (RAPs) within solid tumors. The invention thus provides a method for enzyme-dependent, site-specific, in vivo precipitation of a water-soluble RAP within solid tumors, e.g., for diagnostic or therapeutic purposes.

In certain embodiments, the RAP is hydrolyzed to a water-insoluble RadioActive Drug (RAD) by one or more enzymes that is/are specifically overexpressed on the exterior surface of tumor-cell membranes and is/are minimally expressed on normal cells. In other embodiments, the enzyme or enzymes is/are specifically over-secreted by tumor cells and is/are minimally secreted by normal cells. In both situations, the precipitated water-insoluble RAD is specifically and irreversibly entrapped within the extracellular space, e.g., of solid tumors.

Thus, in one aspect, the invention provides a method of localizing a substantially water-insoluble drug within the extracellular space of tumor tissue in a subject. The method includes the step of administering a water-soluble prodrug to the subject, wherein the prodrug comprises a prosthetic group, wherein the prosthetic group is cleavable by an enzyme, whereby cleavage of the prosthetic group from the prodrug yields the substantially water-insoluble drug, such that the substantially water-insoluble drug is localized within the extracellular space of tumor tissue in a subject.

In another aspect, the invention provides a method of localizing a substantially water-insoluble radioactive drug within the extracellular space of tumor tissue in a subject. The method includes the step of administering a water-soluble radioactive prodrug to the subject, wherein the prodrug comprises at least a first prosthetic group and a second prosthetic group, wherein the first prosthetic group is cleavable by a first enzyme and the second prosthetic group is cleavable by a second enzyme, whereby cleavage of the first and second prosthetic groups from the prodrug yields the substantially water-insoluble radioactive drug, such that the substantially water-insoluble radioactive drug is localized within the extracellular space of tumor tissue in a subject.

In another aspect, the invention provides a method of localizing a substantially water-insoluble radioactive drug within the extracellular space of tumor tissue in a subject, wherein a water-soluble radioactive prodrug comprises at least a first prosthetic group and a second prosthetic group, wherein the first prosthetic group and the second prosthetic groups are both cleavable by a single enzyme, whereby cleavage of the first and second prosthetic groups from the radioactive prodrug yields the substantially water-insoluble radioactive drug, such that the substantially water-insoluble radioactive drug is localized within the extracellular space of tumor tissue in a subject.

In another aspect, the invention provides a method of localizing a substantially water-insoluble radioactive drug within the extracellular space of tumor tissue in a subject, the method comprising administering a water-soluble radioactive prodrug to the subject, wherein the water-soluble radioactive prodrug comprises at least a first prosthetic group and a second prosthetic group, wherein the first prosthetic group is cleavable by a first enzyme and the second prosthetic group is independently cleavable by a second enzyme, whereby cleavage of the first and second prosthetic groups from the prodrug yields the substantially water-insoluble radioactive drug, such that the substantially water-insoluble radioactive drug is localized within the extracellular space of tumor tissue in a subject.

In still another aspect, the invention provides a method of localizing a substantially water-insoluble radioactive drug within the extracellular space of tumor tissue in a subject, the method comprising administering a water-soluble radioactive prodrug to the subject, wherein the water-soluble radioactive prodrug comprises at least a first prosthetic group and a second prosthetic group, wherein the first prosthetic group is cleavable first by a first enzyme and the second prosthetic group is cleavable by a second enzyme after cleavage of the first prosthetic group, whereby cleavage of the first and second prosthetic groups from the prodrug yields the substantially water-insoluble radioactive drug, such that the substantially water-insoluble radioactive drug is localized within the extracellular space of tumor tissue in a subject.

In yet another aspect, the invention provides a method of localizing a substantially water-insoluble radioactive drug within the extracellular space of tumor tissue in a subject, the method comprising administering a water-soluble radioactive prodrug to the subject, wherein the water-soluble radioactive prodrug comprises at least a first prosthetic group, a second prosthetic group, and a third prosthetic group, wherein the first prosthetic group is cleavable first by a first enzyme, the second prosthetic group is subsequently cleavable by a second enzyme, and the third prosthetic group is subsequently cleaved by a third enzyme, whereby cleavage of the first, second, and third prosthetic groups from the prodrug yields the substantially water-insoluble radioactive drug, such that the substantially water-insoluble radioactive drug is localized within the extracellular space of tumor tissue in a subject.

In a still further aspect, the invention provides a method of localizing a substantially water-insoluble radioactive drug within the extracellular space of tumor tissue in a subject, the method comprising administering a water-soluble radioactive prodrug to the subject, wherein the water-soluble radioactive prodrug comprises at least a first prosthetic group, a second prosthetic group, a third prosthetic group, and a fourth prosthetic group, wherein the first and fourth prosthetic groups are both cleavable first by a first enzyme, and the second and third prosthetic groups are both subsequently cleavable by a second enzyme, whereby cleavage of the first, second, third, and fourth prosthetic groups from the prodrug yields the substantially water-insoluble radioactive drug, such that the substantially water-insoluble radioactive drug is localized within the extracellular space of tumor tissue in a subject.

In another aspect, the invention provides a method of localizing a substantially water-insoluble radioactive drug within the extracellular space of tumor tissue in a subject, the method comprising administering a water-soluble radioactive prodrug to the subject, wherein the water-soluble radioactive prodrug comprises at least a first prosthetic group, a second prosthetic group, a third prosthetic group, a fourth prosthetic group, a fifth prosthetic group, and a sixth prosthetic group, wherein the first and sixth prosthetic groups are both cleavable first by a first enzyme, the second and fifth prosthetic groups are both subsequently cleavable by a second enzyme, and the third and fourth prosthetic groups are subsequently cleaved by a third enzyme, whereby cleavage of the first, second, third, fourth, fifth, and sixth prosthetic groups from the prodrug yields the substantially water-insoluble radioactive drug, such that the substantially water-insoluble radioactive drug is localized within the extracellular space of tumor tissue in a subject.

In yet another aspect, the invention provides a method of localizing a substantially water-insoluble radioactive drug within the extracellular space of tumor tissue in a subject. The method includes the step of administering a water-soluble radioactive prodrug to the subject, wherein the prodrug has more one or more substituents that enhance its binding energy to the enzyme. The prodrug also comprises a prosthetic group that is cleavable by an enzyme, whereby cleavage of the prosthetic group from the prodrug yields the substantially water-insoluble radioactive drug, such that the substantially water-insoluble radioactive drug is localized within the extracellular space of tumor tissue in a subject.

In another aspect, the invention provides a method of localizing a substantially water-insoluble radioactive drug within the extracellular space of tumor tissue in a subject. The method includes the step of administering an enzyme-ligand (tumor-specific) to the subject prior to administering a water-soluble radioactive prodrug to the subject, wherein the prosthetic group(s) of the prodrug is/are cleaved by the pre-targeted enzyme(s), whereby cleavage of the prosthetic group(s) from the prodrug yields the substantially water-insoluble radioactive drug, such that the substantially water-insoluble radioactive drug is localized within the extracellular space of tumor tissue in a subject.

In another aspect, the invention provides a method of localizing a substantially water-insoluble radioactive drug within the extracellular space of tumor tissue in a subject. The method includes the step of administering an enzyme-antibody (tumor-specific) to the subject prior to administering a water-soluble radioactive prodrug to the subject, wherein the prosthetic group(s) of the prodrug is/are cleaved by the pre-targeted enzyme(s), whereby cleavage of the prosthetic group(s) from the prodrug yields the substantially water-insoluble radioactive drug, such that the substantially water-insoluble radioactive drug is localized within the extracellular space of tumor tissue in a subject.

In another aspect, the invention provides a method of localizing a substantially water-insoluble radioactive drug within the extracellular space of tumor tissue in a subject. The method includes the step of administering a DNA molecule, plasmid, liposomes or nanoparticles containing these molecules, virus, or bacteria, to the subject prior to administering a water-soluble radioactive prodrug to the subject, wherein the pre-targeted moieties transfect the tumor cells and leads them to overexpress one or more hydrolases extracellularly, and wherein the prosthetic group(s) of the prodrug is/are cleaved by the enzyme(s) expressed by the tumor cells, whereby cleavage of the prosthetic group(s) from the prodrug yields the substantially water-insoluble radioactive drug, such that the substantially water-insoluble radioactive drug is localized within the extracellular space of tumor tissue in a subject. In certain embodiments, the enzyme(s) is/are pre-targeted to the tumor cells. In certain embodiments, the enzyme(s) is/are targeted using a ligand that binds to a receptor expressed by tumor cells.

In certain embodiments of some of the above aspects, at least one of the first and/or second (and/or third, if present) enzymes is present in the extracellular space of the tumor tissue. In certain embodiments, at least one of the first and second (and/or third, if present) enzymes is produced naturally by cells of the tumor tissue. In certain embodiments, at least one of the first and second enzymes (and/or third, if present) is unique to tumor cells or is produced at concentrations that are higher in tumor cells than in normal tissues. In certain embodiments, at least one of the first, second, and/or third enzymes is selected from the group of peptidases, proteinase/proteases, kallikreins, sulfatases, and phosphatases including, but not limited to, prostate specific antigen, matrix metalloproteinases, serine proteinases/proteases, cysteine proteinases/proteases, aspartic proteinases/proteases, threonine proteinase/protease, glutamic acid proteinase/protease, aminopeptidases, carboxypeptidases, dipeptidases, tripeptidases, peptidyle peptidases, guanidinobenzoatase, prostate specific membrane antigen, alkaline phosphatase, prostatic acid phosphatase, and sulfatase (e.g., extracellular human sulfatase-1). In certain embodiments, the first and second enzymes are the same. In certain embodiments, the first and second (and third, if present) prosthetic groups are cleaved sequentially; in certain embodiments, the first and second (and third, if present) prosthetic groups are cleaved substantially simultaneously.

In another aspect, the invention provides a compound or salt represented by the formula:

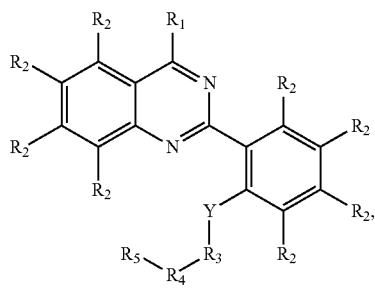

(I)

in which
R$_1$ is H, COOH, amino, mono- or di(C$_1$-C$_6$alkyl)amino, C$_1$-C$_8$alkyl, C$_2$-C$_8$alkenyl, C$_2$-C$_8$alkynyl, C$_3$-C$_8$cycloalkyl, aryl, halogen, C$_1$-C$_8$alkoxy, nitro, or cyano; or R$_1$ is a radionuclide or a moiety containing, or capable of complexing with, a radionuclide;

R$_2$ is, independently for each occurrence, H, hydroxy, COOH, amino, mono- or di(C$_1$-C$_6$alkyl)amino, C$_1$-C$_8$alkyl, C$_2$-C$_8$alkenyl, C$_2$-C$_8$alkynyl, C$_3$-C$_8$cycloalkyl, aryl, halogen, C$_1$-C$_8$alkoxy, nitro, cyano, or a radionuclide or a moiety containing, or capable of complexing with, a radionuclide;

R$_3$ and R$_4$ are each independently a direct bond or a group which can be cleaved by an enzyme, provided that at least one of R$_3$ and R$_4$ is a group which can be cleaved by an enzyme;

R$_5$ is a group which can be cleaved by an enzyme; and

Y is O, S or NH or N(alkyl) (e.g., NCH$_3$);

provided that at least one occurrence of R$_1$ or R$_2$ is a radionuclide or a moiety containing, or capable of complexing with, a radionuclide;

or a pharmaceutically acceptable salt thereof.

In certain embodiments, R$_3$ and R$_4$ are each independently a group which can be cleaved by an enzyme.

In certain embodiments, the compound or salt can be represented by the formula:

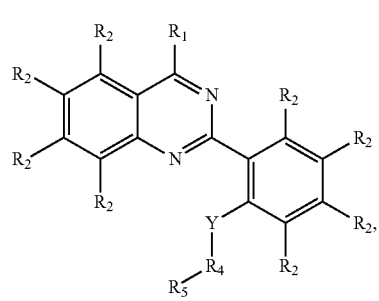

(II)

in which Y, R$_1$, R$_2$, R$_4$, and R$_5$ are as defined for Formula I, and in which at least one occurrence of R$_1$ or R$_2$ is a radionuclide or a moiety containing, or capable of complexing with, a radionuclide.

In certain embodiments, the compound or salt can be represented by the formula:

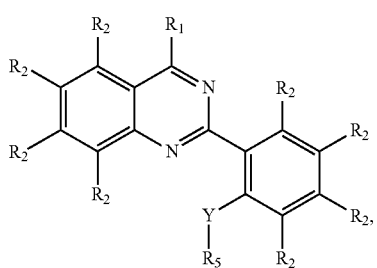

(III)

in which Y, R$_1$, R$_2$, and R$_5$ are as defined for Formula I, and in which at least one occurrence of R$_1$ or R$_2$ is a radionuclide or a moiety containing, or capable of complexing with, a radionuclide.

In certain embodiments, the compound or salt can be represented by the formula:

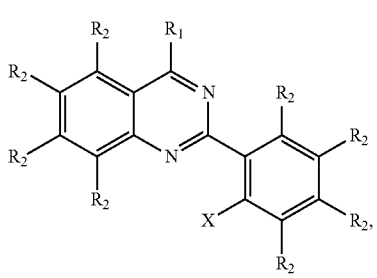

(IV)

in which R$_1$ and R$_2$ are as defined for Formula I; and

X is OH, SH or NH$_2$ or NH(alkyl) (e.g., NHCH$_3$);

provided that at least one occurrence of R$_1$ or R$_2$ is a radionuclide or a moiety containing, or capable of complexing with, a radionuclide.

In another aspect, the invention provides a compound or salt represented by the formula:

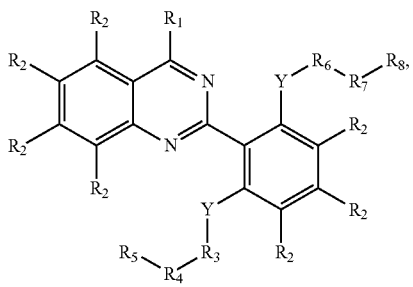

(V)

in which
- $R_1$ is H, COOH, amino, mono- or di($C_1$-$C_6$alkyl)amino, halogen, $C_1$-$C_8$alkyl, $C_2$-$C_8$alkenyl, $C_2$-$C_8$alkynyl, $C_3$-$C_8$cycloalkyl, aryl, $C_1$-$C_8$alkoxy, nitro, or cyano; or $R_1$ is a radionuclide or a moiety containing, or capable of complexing with, a radionuclide;
- $R_2$ is, independently for each occurrence, H, hydroxy, COOH, amino, mono- or di($C_1$-$C_6$alkyl)amino, $C_1$-$C_8$alkyl, $C_2$-$C_8$alkenyl, $C_2$-$C_8$alkynyl, $C_3$-$C_8$cycloalkyl, aryl, halogen, $C_1$-$C_8$alkoxy, nitro, cyano, or a radionuclide or a moiety containing, or capable of complexing with, a radionuclide;
- $R_3$, $R_4$, $R_6$ and $R_7$ are each independently a direct bond or a group which can be cleaved by an enzyme;
- $R_5$ and $R_8$ are each independently a group which can be cleaved by an enzyme; and
- Y is, independently for each occurrence, O, S or NH or N(alkyl) (e.g., $NCH_3$);
- provided that at least one occurrence of $R_1$ or $R_2$ is a radionuclide or a moiety containing, or capable of complexing with, a radionuclide;

or a pharmaceutically acceptable salt thereof.

In certain embodiments, $R_3$ and $R_4$ are each independently a group which can be cleaved by an enzyme. In certain embodiments, $R_6$ and $R_7$ are each independently a group which can be cleaved by an enzyme. In certain embodiments, $R_3$ and $R_6$ are each independently a group which can be cleaved by an enzyme.

In certain embodiments, the compound or salt can be represented by the formula:

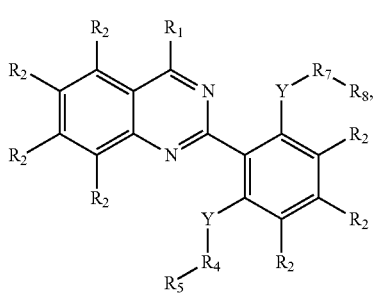

(VI)

in which Y, $R_1$, $R_2$, $R_4$, $R_5$, $R_7$, and $R_8$ are as defined for Formula V, and in which at least one occurrence of $R_1$ or $R_2$ is a radionuclide or a moiety containing, or capable of complexing with, a radionuclide.

In certain embodiments, the compound or salt can be represented by the formula:

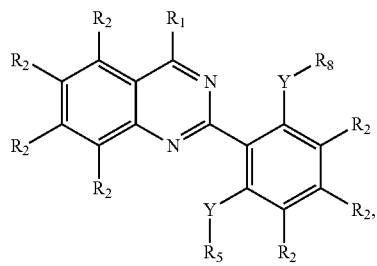

(VII)

in which Y, $R_1$, $R_2$, $R_5$, and $R_8$ are as defined for Formula V and in which at least one occurrence of $R_1$ or $R_2$ is a radionuclide or a moiety containing, or capable of complexing with, a radionuclide.

In certain embodiments, the compound or salt can be represented by the formula:

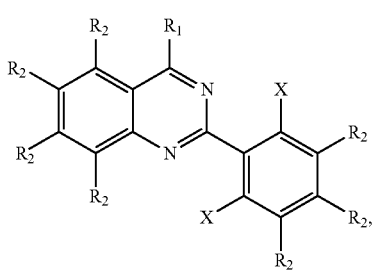

(VIII)

in which $R_1$ and $R_2$ are as defined for Formula V, in which at least one occurrence of $R_1$ or $R_2$ is a radionuclide or a moiety containing, or capable of complexing with, a radionuclide; and X is independently OH, SH or $NH_2$ or NH(alkyl) (e.g., $NHCH_3$).

In another aspect, the invention provides a compound or salt represented by the formula:

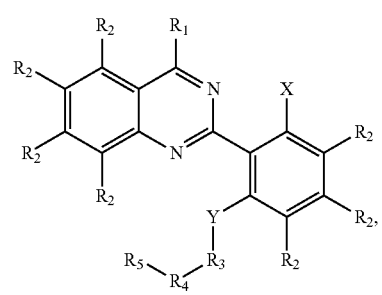

(IX)

in which
- $R_1$ is H, COOH, amino, mono- or di($C_1$-$C_6$alkyl)amino, $C_1$-$C_8$alkyl, $C_2$-$C_8$alkenyl, $C_2$-$C_8$alkynyl, $C_3$-$C_8$cycloalkyl, aryl, halogen, $C_1$-$C_8$alkoxy, nitro, or cyano; or $R_1$ is a radionuclide or a moiety containing, or capable of complexing with, a radionuclide;
- $R_2$ is, independently for each occurrence, H, hydroxy, COOH, amino, mono- or di($C_1$-$C_6$alkyl)amino, $C_1$-$C_8$alkyl, $C_2$-$C_8$alkenyl, $C_2$-$C_8$alkynyl, $C_3$-$C_8$cycloalkyl, aryl, halogen, $C_1$-$C_8$alkoxy, nitro, cyano, or a radionuclide or a moiety containing, or capable of complexing with, a radionuclide;

$R_3$ and $R_4$ are each independently a direct bond or a group which can be cleaved by an enzyme, provided that at least one of $R_3$ and $R_4$ is a group which can be cleaved by an enzyme;

$R_5$ is a group which can be cleaved by an enzyme;

Y is O, S or NH or N(alkyl) (e.g., $NCH_3$); and

X is OH, SH or $NH_2$ or NH(alkyl) (e.g., $NHCH_3$);

provided that at least one occurrence of $R_1$ or $R_2$ is a radionuclide or a moiety containing, or capable of complexing with, a radionuclide;

or a pharmaceutically acceptable salt thereof.

In certain embodiments, $R_3$ and $R_4$ are each independently a group which can be cleaved by an enzyme.

In certain embodiments, the compound or salt can be represented by the formula:

(X)

in which Y, $R_1$, $R_2$, $R_4$, and $R_5$ are as defined for Formula IX, in which at least one occurrence of $R_1$ or $R_2$ is a radionuclide or a moiety containing, or capable of complexing with, a radionuclide; and X is OH, SH or $NH_2$ or NH(alkyl) (e.g., $NHCH_3$).

In certain embodiments, the compound or salt can be represented by the formula:

(XI)

in which Y, $R_1$, $R_2$, and $R_5$ are as defined for Formula IX; and

X is independently OH, SH or $NH_2$ or NH(alkyl) (e.g., $NHCH_3$) and in which at least one occurrence of $R_1$ or $R_2$ is a radionuclide or a moiety containing, or capable of complexing with, a radionuclide.

In another aspect, the invention provides a compound or salt represented by the formula:

(XII)

in which $R_2$ is, independently for each occurrence, H, hydroxy, COOH, amino, mono- or di($C_1$-$C_6$alkyl)amino, $C_1$-$C_8$alkyl, $C_2$-$C_8$alkenyl, $C_2$-$C_8$alkynyl, $C_3$-$C_8$cycloalkyl, aryl, halogen, $C_1$-$C_8$alkoxy, nitro, cyano, or a radionuclide or a moiety containing, or capable of complexing with, a radionuclide;

$R_3$ and $R_4$ are each independently a direct bond or a group which can be cleaved by an enzyme, provided that at least one of $R_3$ and $R_4$ is a group which can be cleaved by an enzyme;

$R_5$ is a group which can be cleaved by an enzyme; and

Y is O, S or NH or N(alkyl) (e.g., $NCH_3$);

provided that at least one occurrence of $R_2$ is a radionuclide or a moiety containing, or capable of complexing with, a radionuclide;

or a pharmaceutically acceptable salt thereof.

In certain embodiments, $R_3$ and $R_4$ are each independently a group which can be cleaved by an enzyme.

In certain embodiments, the compound or salt can be represented by the formula:

(XIII)

in which Y, $R_2$, $R_4$, and $R_5$ are as defined for Formula XII and in which at least one occurrence of $R_2$ is a radionuclide or a moiety containing, or capable of complexing with, a radionuclide.

In certain embodiments, the compound or salt can be represented by the formula:

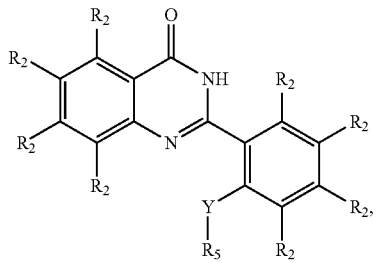
(XIV)

in which Y, $R_2$, and $R_5$ are as defined for Formula XII and in which at least one occurrence of $R_2$ is a radionuclide or a moiety containing, or capable of complexing with, a radionuclide.

In certain embodiments, the compound or salt can be represented by the formula:

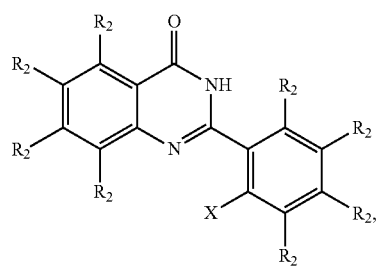
(XV)

in which $R_2$ is as defined for Formula XII and in which at least one occurrence of $R_2$ is a radionuclide or a moiety containing, or capable of complexing with, a radionuclide; and X is OH, SH or $NH_2$ or NH(alkyl) (e.g., $NHCH_3$).

In another aspect, the invention provides a compound or salt represented by the formula:

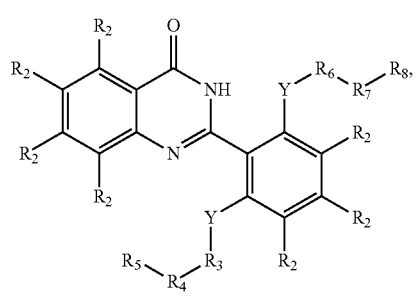
(XVI)

in which
$R_2$ is, independently for each occurrence, H, hydroxy, COOH, amino, mono- or di($C_1$-$C_6$alkyl)amino, $C_1$-$C_8$alkyl, $C_2$-$C_8$alkenyl, $C_2$-$C_8$alkynyl, $C_3$-$C_8$cycloalkyl, aryl, halogen, $C_1$-$C_8$alkoxy, nitro, cyano, or a radionuclide or a moiety containing, or capable of complexing with, a radionuclide;

$R_3$, $R_4$, $R_6$ and $R_7$ are each independently a direct bond or a group which can be cleaved by an enzyme;

$R_5$ and $R_8$ are each independently a group which can be cleaved by an enzyme; and Y is, independently for each occurrence, O, S or NH or N(alkyl) (e.g., $NCH_3$);

provided that at least one occurrence of $R_2$ is a radionuclide or a moiety containing, or capable of complexing with, a radionuclide;

or a pharmaceutically acceptable salt thereof.

In certain embodiments, $R_3$ and $R_4$ are each independently a group which can be cleaved by an enzyme. In certain embodiments, $R_6$ and $R_7$ are each independently a group which can be cleaved by an enzyme. In certain embodiments, $R_3$ and $R_6$ are each independently a group which can be cleaved by an enzyme.

In certain embodiments, the compound or salt can be represented by the formula:

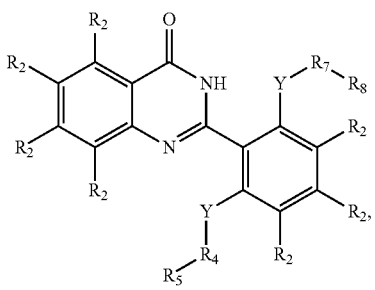
(XVII)

in which Y, $R_2$, $R_4$, $R_5$, $R_7$, and $R_8$ are as defined for Formula XVI and in which at least one occurrence of $R_2$ is a radionuclide or a moiety containing, or capable of complexing with, a radionuclide.

In certain embodiments, the compound or salt can be represented by the formula:

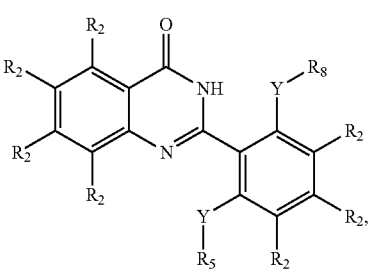
(XVIII)

in which Y, $R_2$, $R_5$, and $R_8$ are as defined for Formula XVI and in which at least one occurrence of $R_2$ is a radionuclide or a moiety containing, or capable of complexing with, a radionuclide.

In certain embodiments, the compound or salt can be represented by the formula:

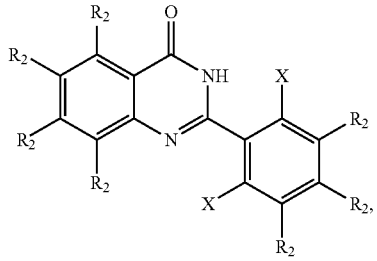

(XIX)

in which $R_2$ is as defined for Formula XVI; and in which at least one occurrence of $R_2$ is a radionuclide or a moiety containing, or capable of complexing with, a radionuclide; and X is OH, SH or $NH_2$ or NH(alkyl) (e.g., $NHCH_3$).

In another aspect, the invention provides a compound or salt represented by the formula:

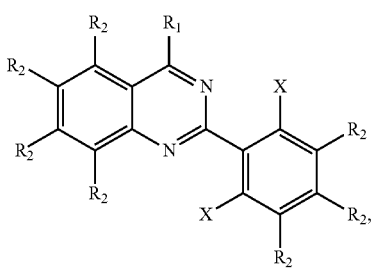

(XX)

in which $R_1$ and $R_2$ have the meanings of the corresponding variable groups of Formula V and in which at least one occurrence of $R_1$ or $R_2$ is a radionuclide or a moiety containing, or capable of complexing with, a radionuclide;

X is OH, SH or $NH_2$ or NH(alkyl) (e.g., $NHCH_3$); and at least one $R_2$ is $R_3$—$R_4$—$R_5$, $R_4$—$R_5$, or $R_5$ as defined for Formula V.

In another aspect, the invention provides a compound or salt represented by the formula:

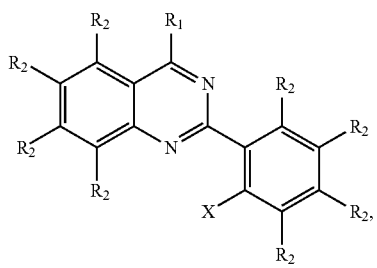

(XXI)

in which $R_1$ and $R_2$ have the meanings of the corresponding variable groups of Formula I; or $R_2$ is independently for each occurrence $R_3$—$R_4$—$R_5$, $R_4$—$R_5$, or $R_5$, or —Y—$R_3$—$R_4$—$R_5$, —Y—$R_4$—$R_5$, or —Y—$R_5$ as defined for Formula I and in which at least one occurrence of $R_1$ or $R_2$ is a radionuclide or a moiety containing, or capable of complexing with, a radionuclide;

X is OH, SH or $NH_2$ or NH(alkyl) (e.g., $NHCH_3$); and at least one $R_2$ is $R_3$—$R_4$—$R_5$, $R_4$—$R_5$, or $R_5$ as defined for Formula I.

In another aspect, the invention provides a compound or salt represented by the formula:

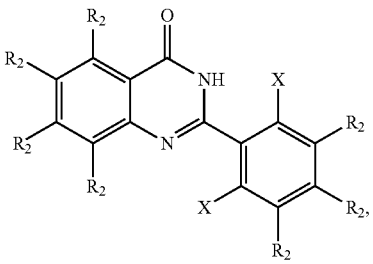

(XXII)

in which $R_2$ has the meanings of the corresponding variable groups of Formula XVI and in which at least one occurrence of $R_2$ is a radionuclide or a moiety containing, or capable of complexing with, a radionuclide; or $R_2$ is independently for each occurrence $R_3$—$R_4$—$R_5$, $R_4$—$R_5$, or $R_5$, or —Y—$R_3$—$R_4$—$R_5$, —Y—$R_4$—$R_5$, or —Y—$R_5$ as, as defined for Formula XVI;

X is independently OH, SH or $NH_2$ or NH(alkyl) (e.g., $NHCH_3$); and at least one $R_2$ is $R_3$—$R_4$—$R_5$, $R_4$—$R_5$, or $R_5$ as defined for Formula XVI.

In another aspect, the invention provides a compound or salt represented by the formula:

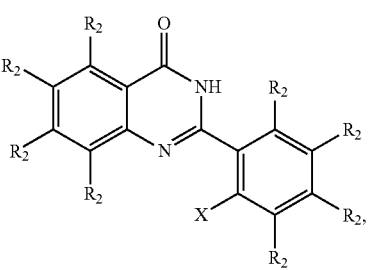

(XXIII)

in which $R_2$ has the meanings of the corresponding variable groups of Formula XII and in which at least one occurrence of $R_2$ is a radionuclide or a moiety containing, or capable of complexing with, a radionuclide; or $R_2$ is independently for each occurrence $R_3$—$R_4$—$R_5$, $R_4$—$R_5$, or $R_5$, or —Y—$R_3$—$R_4$—$R_5$, —Y—$R_4$—$R_5$, or —Y—$R_5$ as defined for Formula XII;

X is OH, SH or $NH_2$ or NH(alkyl) (e.g., $NHCH_3$); and at least one $R_2$ is $R_3$—$R_4$—$R_5$, $R_4$—$R_5$, or $R_5$ as defined for Formula XII.

In certain embodiments of a compound or salt of Formulae V and XVI, $R_3$, $R_4$, $R_6$, and $R_7$ are each a direct bond. In certain embodiments of Formulae V-VII and XVI-XVIII, at least one of $R_5$ and $R_8$ is a group which can be cleaved by an enzyme. In certain embodiments of Formulae V-VII and XVI-XVIII, one of $R_5$ and $R_8$ is H and the other is a group which can be cleaved by an enzyme. In certain embodiments, $R_5$ and $R_8$ are each a group which can be cleaved by an enzyme. In certain embodiments, $R_5$ and $R_8$ are different. In certain embodiments, $R_5$ and $R_8$ can be cleaved by the same enzyme. In certain embodiments, $R_5$ and $R_8$ are the same.

In certain embodiments of a compound or salt of Formulae V and XVI, $R_3$, $R_4$, $R_5$, and $R_6$ are each independently a direct bond. In certain embodiments, $R_3$, $R_4$, $R_5$, $R_6$, $R_7$, and $R_8$ are each a group which can be cleaved by an enzyme. In certain embodiments, one of $R_2$, $R_3$, $R_4$, $R_5$, $R_6$, and $R_7$ is a H and the others are each a group which can be cleaved by an enzyme. In certain embodiments, $R_5$ and $R_8$ are different and each can be cleaved by a different enzyme. In certain embodiments, $R_3$ and $R_6$ are different and each can be cleaved by a different enzyme. In certain embodiments, $R_4$ and $R_7$ are different and each can be cleaved by a different enzyme. In certain embodiments, $R_4$ and $R_7$ are the same and each can be cleaved by the same enzyme. In certain embodiments, $R_3$ and $R_6$ are the same and each can be cleaved by the same enzyme. In certain embodiments, $R_5$ and $R_8$ are the same and each can be cleaved by the same enzyme.

In certain embodiments, the compound or salt can be represented by the formula:

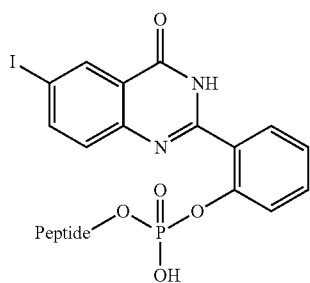

(XXIV)

wherein Peptide is a peptide or polypeptide chain having at least three amino acid residues and having a sequence that is cleavable by a peptidase or a proteinase; and $PO_4$ is a group that is cleavable by a phosphatase after cleavage of the Peptide.

In another embodiment, the compound or salt can be represented by the formula:

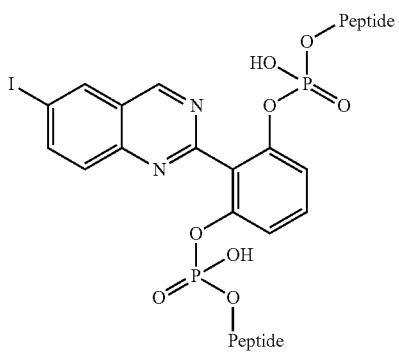

(XXV)

wherein Peptide is independently a peptide or polypeptide chain having at least three amino acid residues and having a sequence that is cleavable by a peptidase or a proteinase. In preferred embodiments of Formula XXV, the phosphate group is cleavable by a phosphatase after cleavage of the Peptide.

In another embodiment, the compound or salt can be represented by the formula:

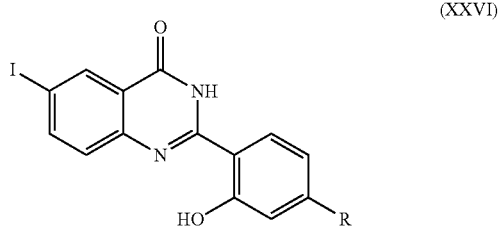

(XXVI)

wherein I is a radioisotope of iodine and

R is:

a peptide or polypeptide chain having at least three amino acid residues and having a sequence that is cleavable by a peptidase or a proteinase; or a phosphate or phosphate ester that is cleavable by a phosphatase; or a sulfate or sulfate ester that is cleavable by a sulfatase.

In another embodiment, the compound or salt can be represented by the formula:

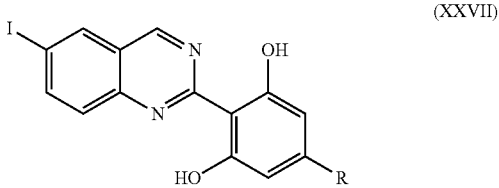

(XXVII)

wherein I is a radioisotope of iodine and

R is:

a peptide or polypeptide chain having at least three amino acid residues and having a sequence that is cleavable by a peptidase or a proteinase; or a phosphate or phosphate ester that is cleavable by a phosphatase; or a sulfate or sulfate ester that is cleavable by a sulfatase.

In another aspect, the invention provides a compound represented by any of the Formulae XXVIII-XXXIX:

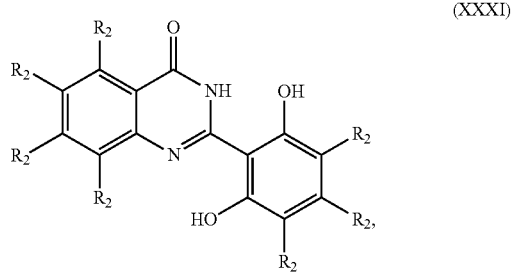

(XXXI)

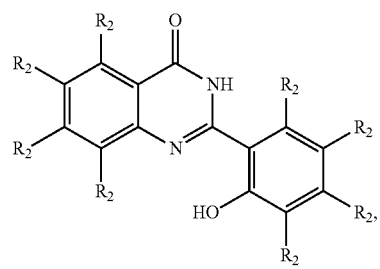
(XXX)

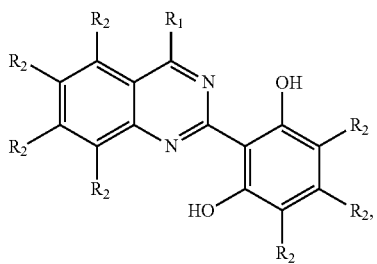
(XXVIII)

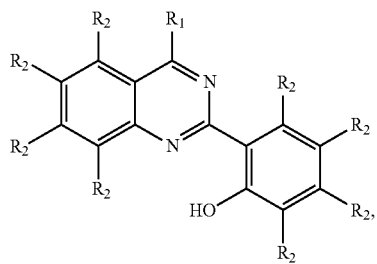
(XXIX)

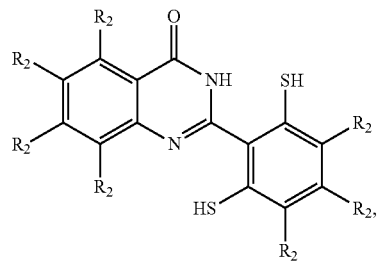
(XXXII)

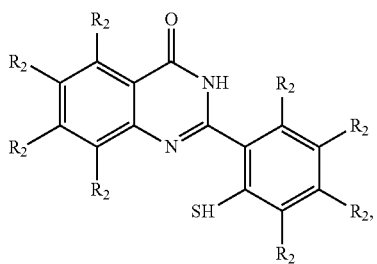
(XXXIII)

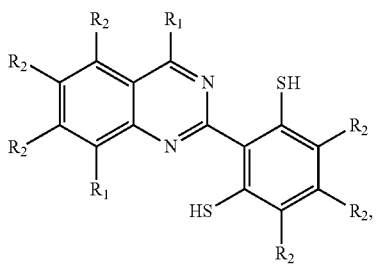
(XXXIV)

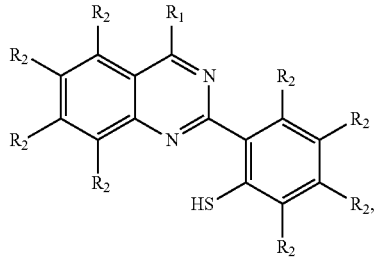
(XXXV)

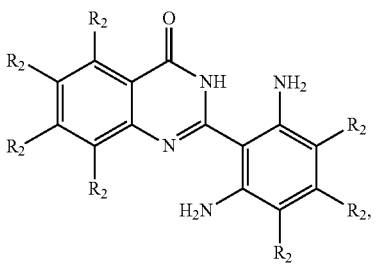
(XXXVI)

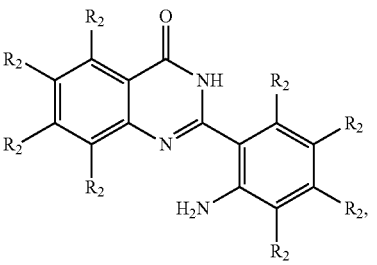
(XXXVII)

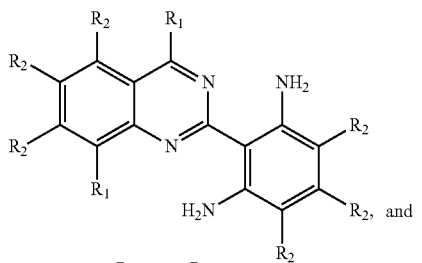
(XXXVIII)

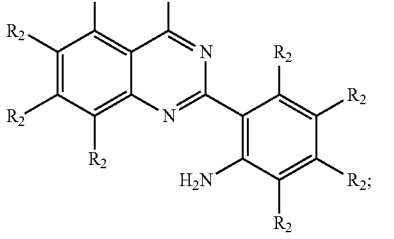
(XXXIX)

in which
$R_1$ is H, COOH, amino, mono- or di($C_1$-$C_6$alkyl)amino, $C_1$-$C_8$alkyl, $C_2$-$C_8$alkenyl, $C_2$-$C_8$alkynyl, $C_3$-$C_8$cycloalkyl, aryl, halogen, $C_1$-$C_8$alkoxy, nitro, or cyano; or $R_1$ is a radionuclide or a moiety containing, or capable of complexing with, a radionuclide; and $R_2$ is, independently for each occurrence, H, hydroxy, COOH, amino, mono- or di($C_1$-$C_6$alkyl)amino, $C_1$-$C_8$alkyl, $C_2$-$C_8$alkenyl, $C_2$-$C_8$alkynyl, $C_3$-$C_8$cycloalkyl, aryl, halogen, $C_1$-$C_8$alkoxy, nitro, cyano, or a radionuclide or a moiety containing, or capable of complexing with, a radionuclide;

or a pharmaceutically acceptable salt thereof.

In certain embodiments of Formulae XXVIII-XXIX, at least one occurrence of $R_1$ or $R_2$ is a radionuclide or a moiety containing, or capable of complexing with, a radionuclide.

In another aspect, the invention provides a method of imaging a tumor in a subject. The method includes the steps of administering a water-soluble radioactive prodrug to the subject, wherein the prodrug comprises at least a first prosthetic group and a detectable radiolabel, wherein the first prosthetic group is cleavable by a first enzyme, whereby cleavage of the first prosthetic group from the prodrug yields the substantially water-insoluble radioactive drug, such that the substantially water-insoluble radioactive drug is localized within the extracellular space of tumor tissue in the subject; and detecting the detectable radiolabel, thereby imaging the tumor (e.g., by SPECT or PET).

In another aspect, the invention provides a method of imaging a tumor in a subject. The method includes the steps of administering a water-soluble radioactive prodrug to the subject, wherein the prodrug comprises at least a first prosthetic group and a second prosthetic group and a detectable radiolabel, wherein the first prosthetic group is cleavable by a first enzyme and the second prosthetic group is cleavable by a second enzyme, whereby cleavage of the first and second prosthetic groups from the prodrug yields the substantially water-insoluble radioactive drug, such that the substantially water-insoluble radioactive drug is localized within the extracellular space of tumor tissue in the subject; and detecting the detectable radiolabel, thereby imaging the tumor (e.g., by SPECT or PET).

In yet another embodiments, the invention provides a method of treating a subject suffering from a tumor. The method includes the steps of administering a water-soluble radioactive prodrug to the subject, wherein the prodrug comprises at least a first prosthetic group and a beta- or alpha-particle-emitting radiolabel, wherein the first prosthetic group is cleavable by a first enzyme, whereby cleavage of the first prosthetic groups from the prodrug yields a substantially water-insoluble radioactive drug, such that the substantially water-insoluble radioactive drug is localized within the extracellular space of tumor tissue in the subject; and allowing the radiolabel to irradiate the tumor tissue, under conditions such that the subject is treated.

In yet another embodiments, the invention provides a method of treating a subject suffering from a tumor. The method includes the steps of administering a water-soluble radioactive prodrug to the subject, wherein the prodrug comprises at least a first prosthetic group and a second prosthetic group and a beta- or alpha-particle-emitting radiolabel, wherein the first prosthetic group is cleavable by a first enzyme and the second prosthetic group is cleavable by a second enzyme, whereby cleavage of the first and second prosthetic groups from the prodrug yields a substantially water-insoluble radioactive drug, such that the substantially water-insoluble radioactive drug is localized within the extracellular space of tumor tissue in the subject; and allowing the radiolabel to irradiate the tumor tissue, under conditions such that the subject is treated.

In still another aspect, the invention provides a pharmaceutical formulation, e.g., a pharmaceutical formulation for imaging or treatment of solid tumors. The pharmaceutical formulation comprises a compound of any of Formulae I-XI, together with a pharmaceutically acceptable carrier.

BRIEF DESCRIPTION OF THE DRAWINGS

FIG. 25 shows the preparation of a compound according to the invention.

DETAILED DESCRIPTION OF THE INVENTION

The present invention relates to radiolabeled compounds capable of localizing specifically and irreversibly within a solid tumor. Such a compound may be a low-molecular-weight species which is preferably (i) readily radiolabeled with a radionuclide such as a gamma- (e.g. [123]I, $^{131}$I, $^{111}$In, $^{99m}$Tc) or positron- (e.g. [124]I, $^{18}$F) emitting diagnostic radionuclides, (ii) easily radiolabeled with energetic electron (e.g. [131]I, $^{90}$Y) or alpha-particle (e.g. [211]At, [213]Bi)-emitting therapeutic radionuclides, (iii) substrate for one or more hydrolyzing enzymes, and (iv) transformed upon hydrolysis by the one or more enzymes to a water-insoluble radioactive drug (RAD) molecule.

In certain embodiments, a compound according to the invention can be hydrolyzed to a water-insoluble radioactive drug (RAD) by one or more enzymes, e.g., preferably by enzymes that are specifically overexpressed on the exterior surface of cells, such as tumor-cell membranes, and are minimally expressed on normal cells; or by enzyme(s) that are specifically over-secreted by tumor cells and minimally secreted by normal cells. The Enzyme-Mediated Cancer Imaging and Therapy (EMCIT) technology results in specific and irreversible entrapment of the precipitated water-insoluble radiopharmaceuticals within the extracellular space of solid tumors.

The compounds and methods of the invention provide several advantages over previously-known compounds and methods. For example, the inventive compounds (both the water-soluble prodrugs and the active insoluble drug form) have very low chemical toxicity. Compounds of Formulae XXVIII-XXX:

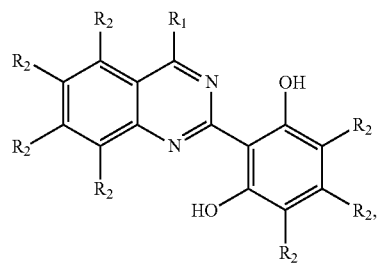

(XXVIII)

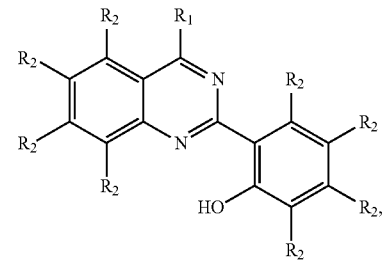

(XXIX)

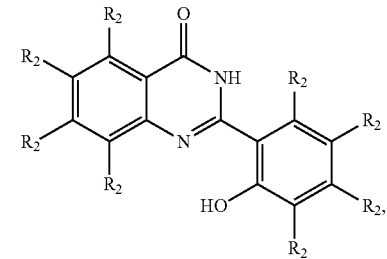

Figure 1:
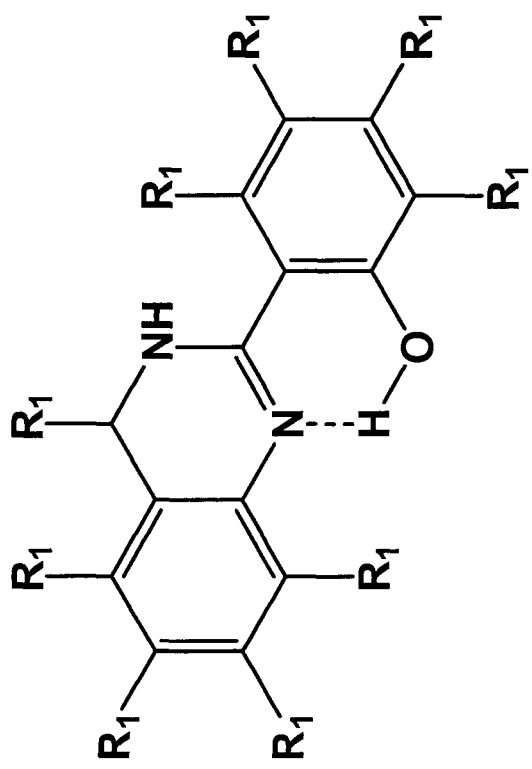
FIG. 1 is a structure of a compound according to certain embodiments of the invention, showing intramolecular hydrogen bond (dotted line) formation within the drug molecule following enzyme-mediated hydrolysis of the prodrug.
Figure 2:
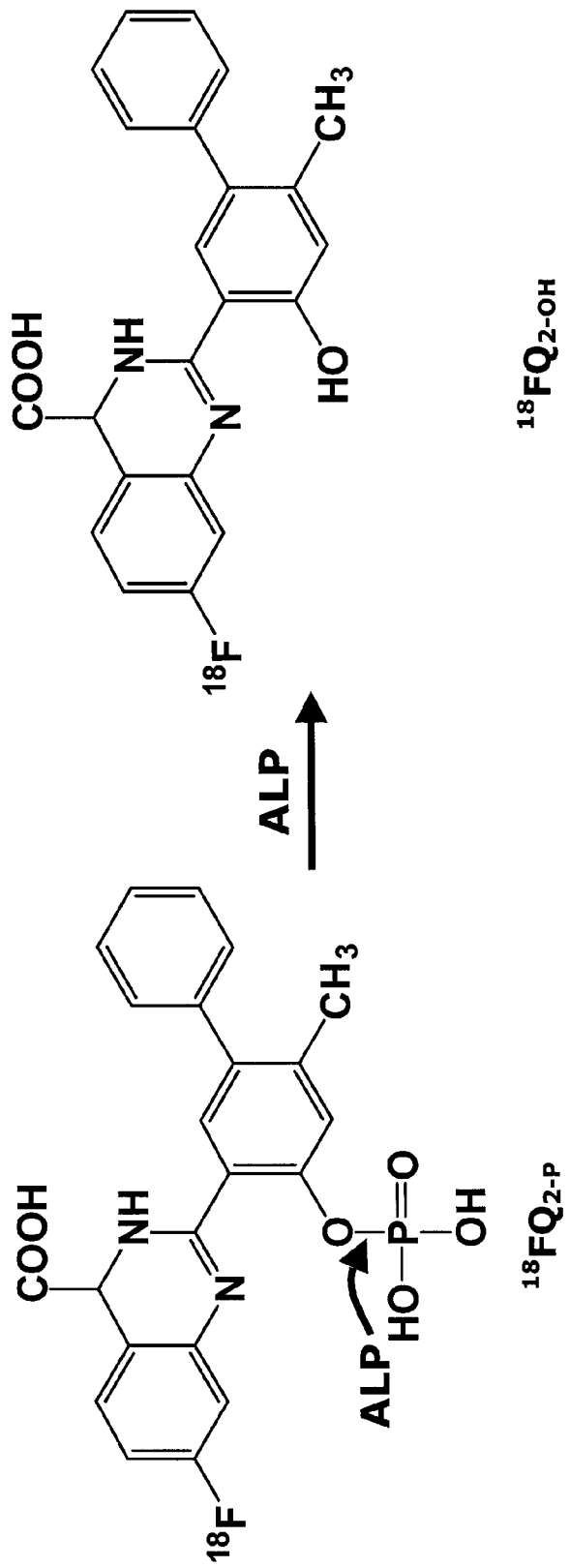
FIG. 2 is a scheme showing one embodiment of a compound of the invention. $^{18}F$=fluorine-18; ALP=alkaline phosphatase.
Figure 3:
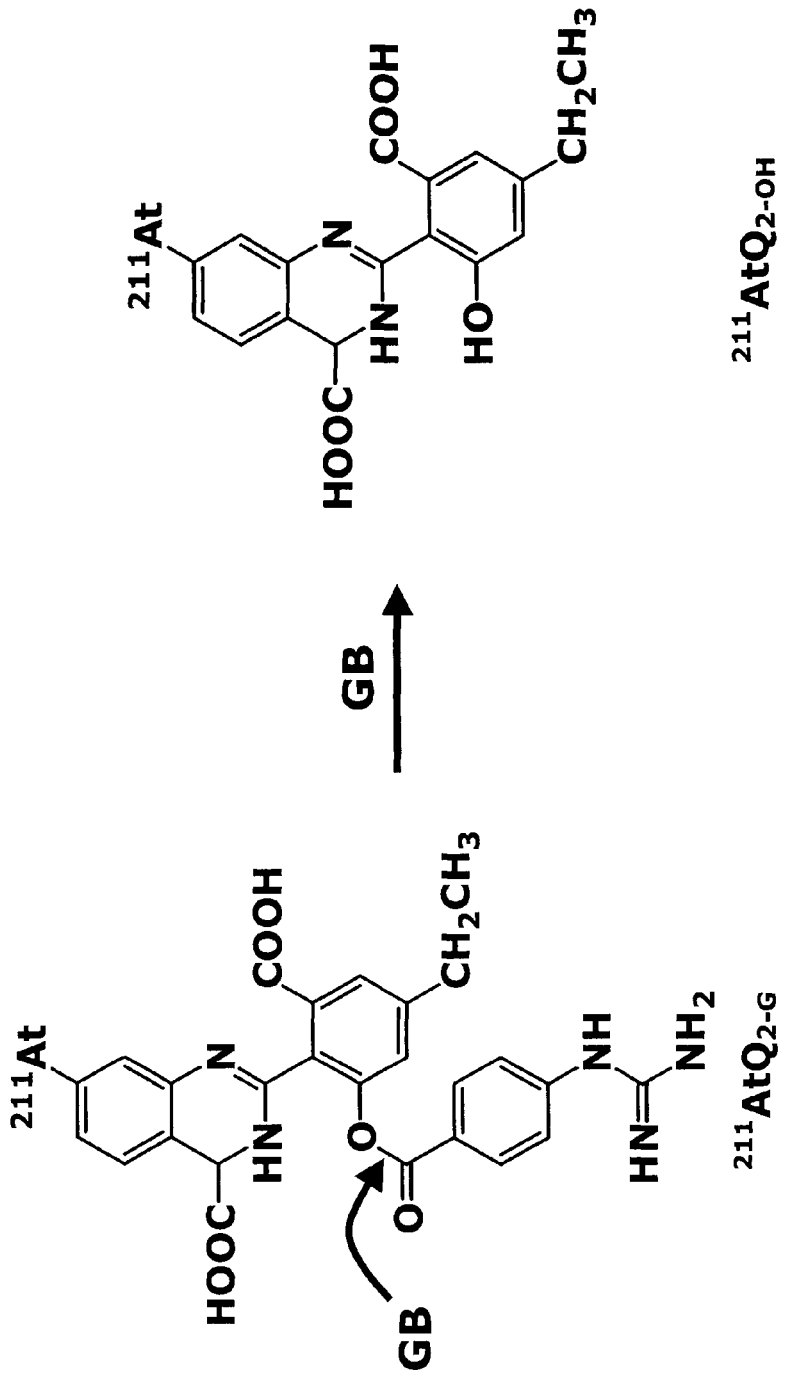
FIG. 3 is a scheme showing one embodiment of a compound of the invention. $^{211}At$=astatine-211; G=guanidinobenzoate; GB=guanidinobenzoatase.
Figure 10:
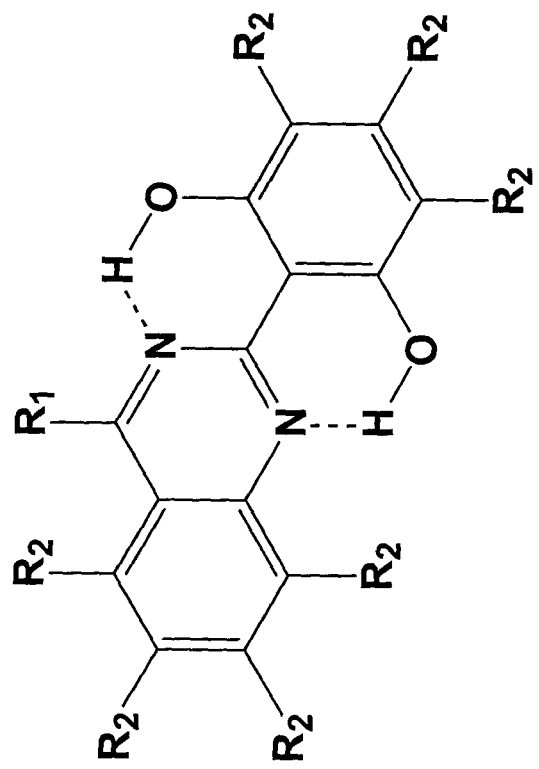
FIG. 10 is a structure of a compound according to certain embodiments of the invention, showing intramolecular hydrogen bond (dotted lines) formation within the drug molecule following enzyme-mediated hydrolysis of the prodrug.
Figure 11:
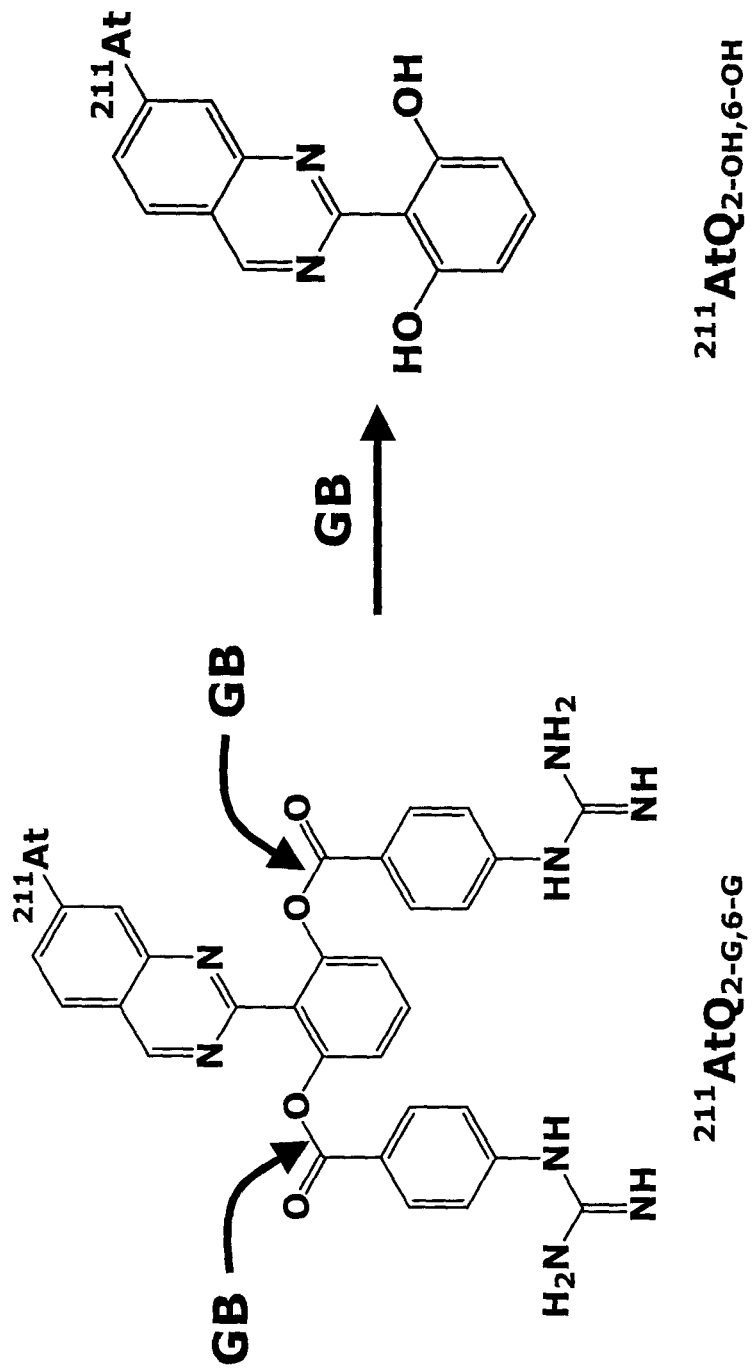
FIG. 11 is a scheme showing one embodiment of a compound of the invention. $^{211}At$=astatine-211; G=guanidinobenzoate; GB=guanidinobenzoatase.
Figure 12:
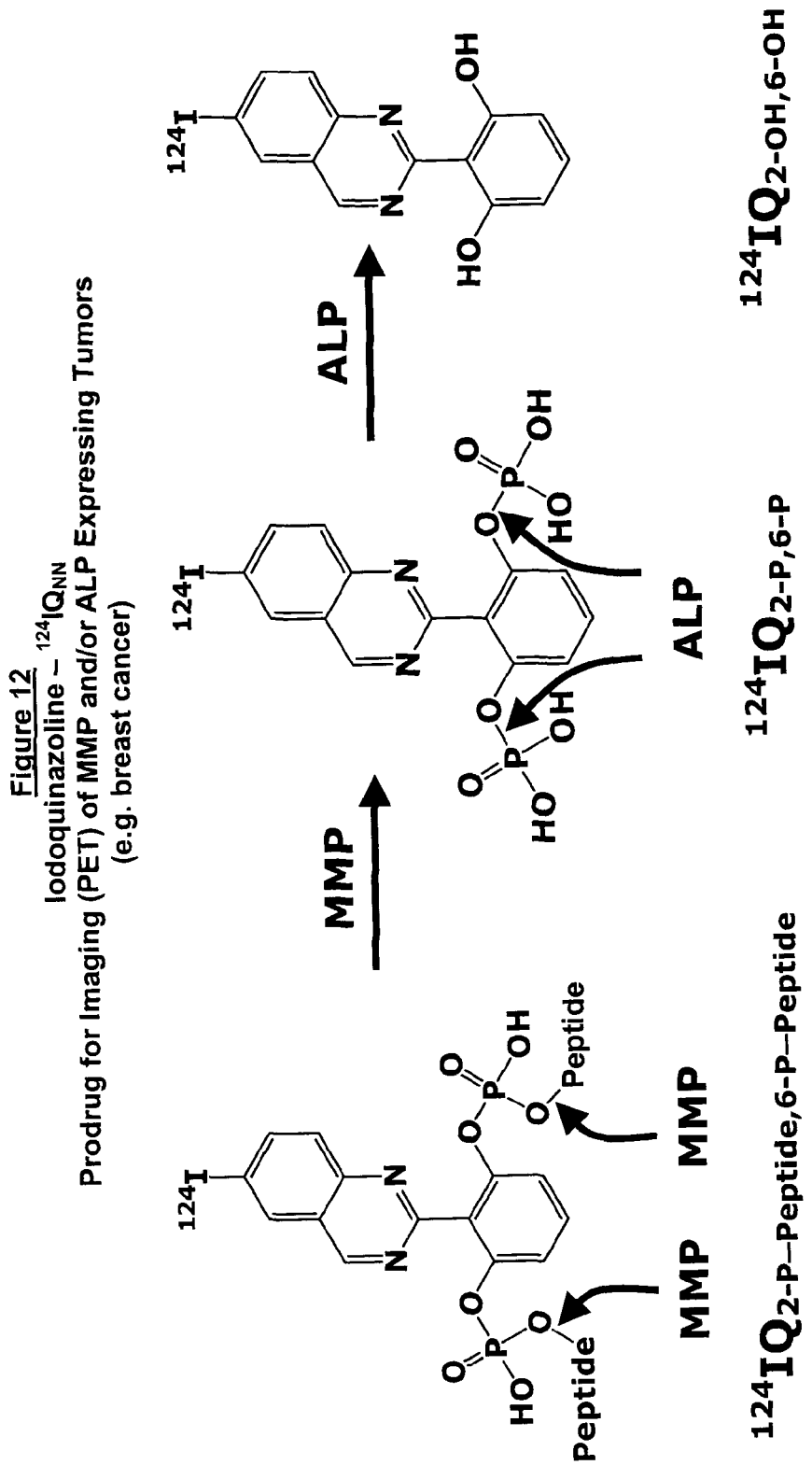
FIG. 12 is a scheme showing one embodiment of a compound of the invention. $^{124}I$=iodine-124; MMP=matrix metalloproteinase; ALP=alkaline phosphatase.
Figure 13:
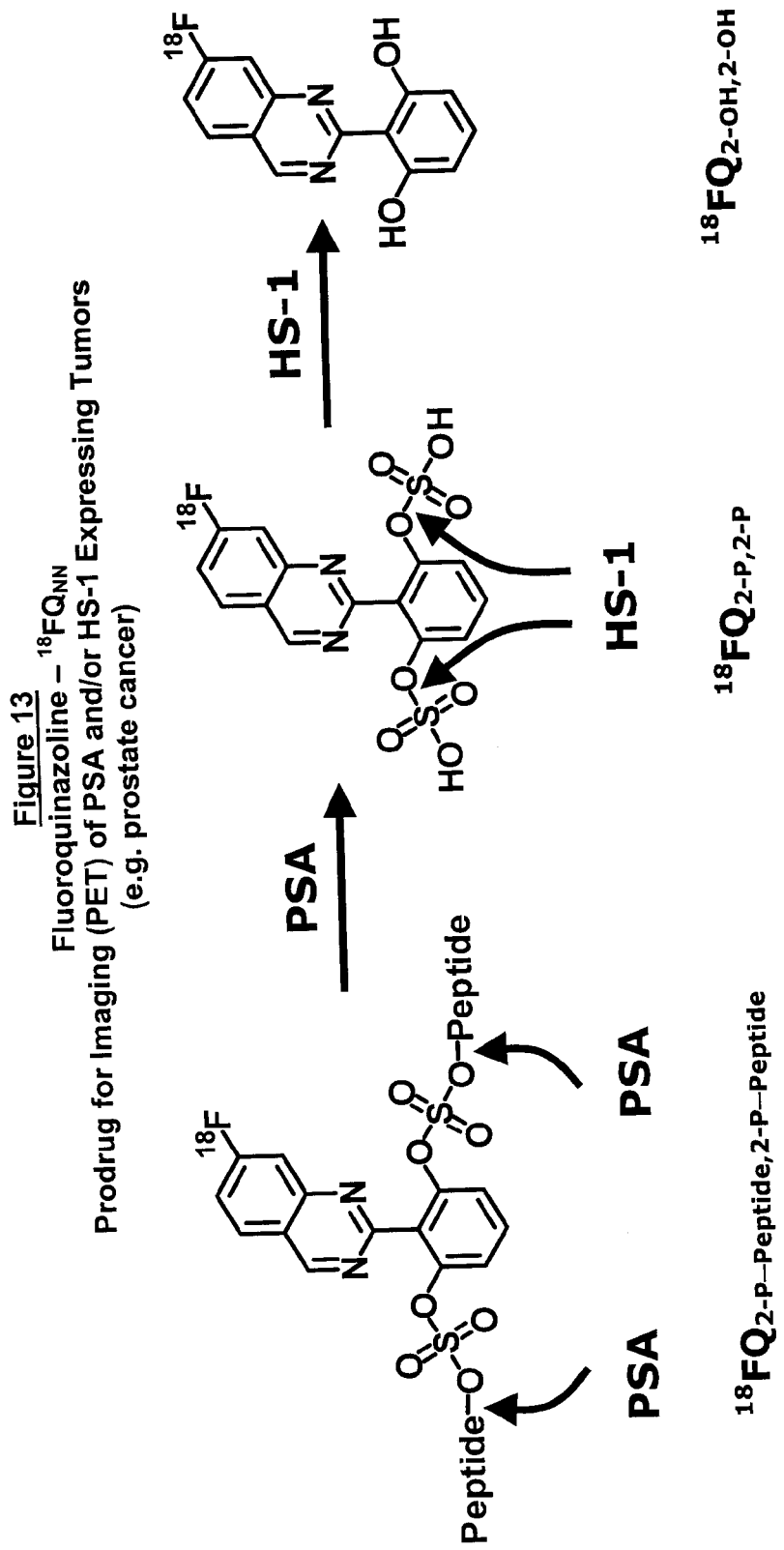
FIG. 13 is a scheme showing one embodiment of a compound of the invention. $^{18}F$=fluorine-18; PSA=prostate specific antigen; HS-1=human sulfatase-1.
Figure 14:
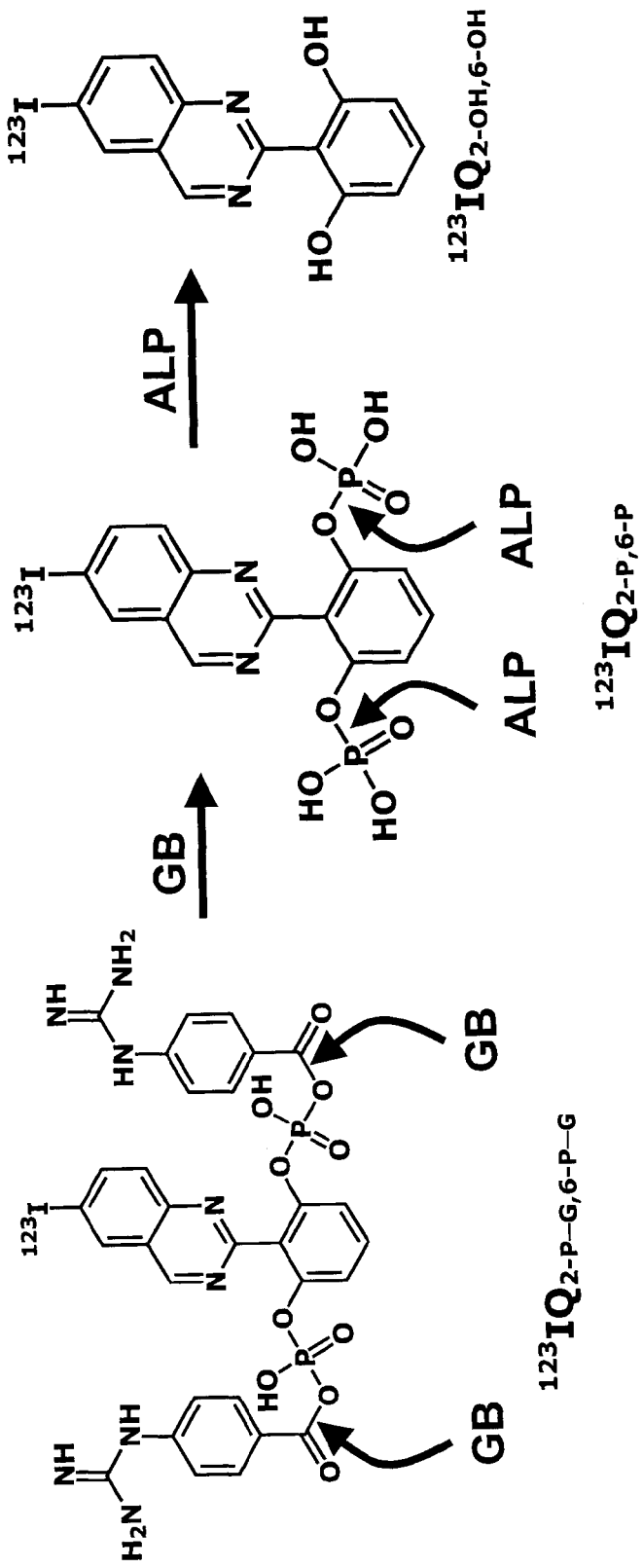
FIG. 14 is a scheme showing one embodiment of a compound of the invention. $^{123}I$=iodine-123; G=guanidinobenzoate; GB=guanidinobenzoatase; ALP=alkaline phosphatase.
Figure 15:
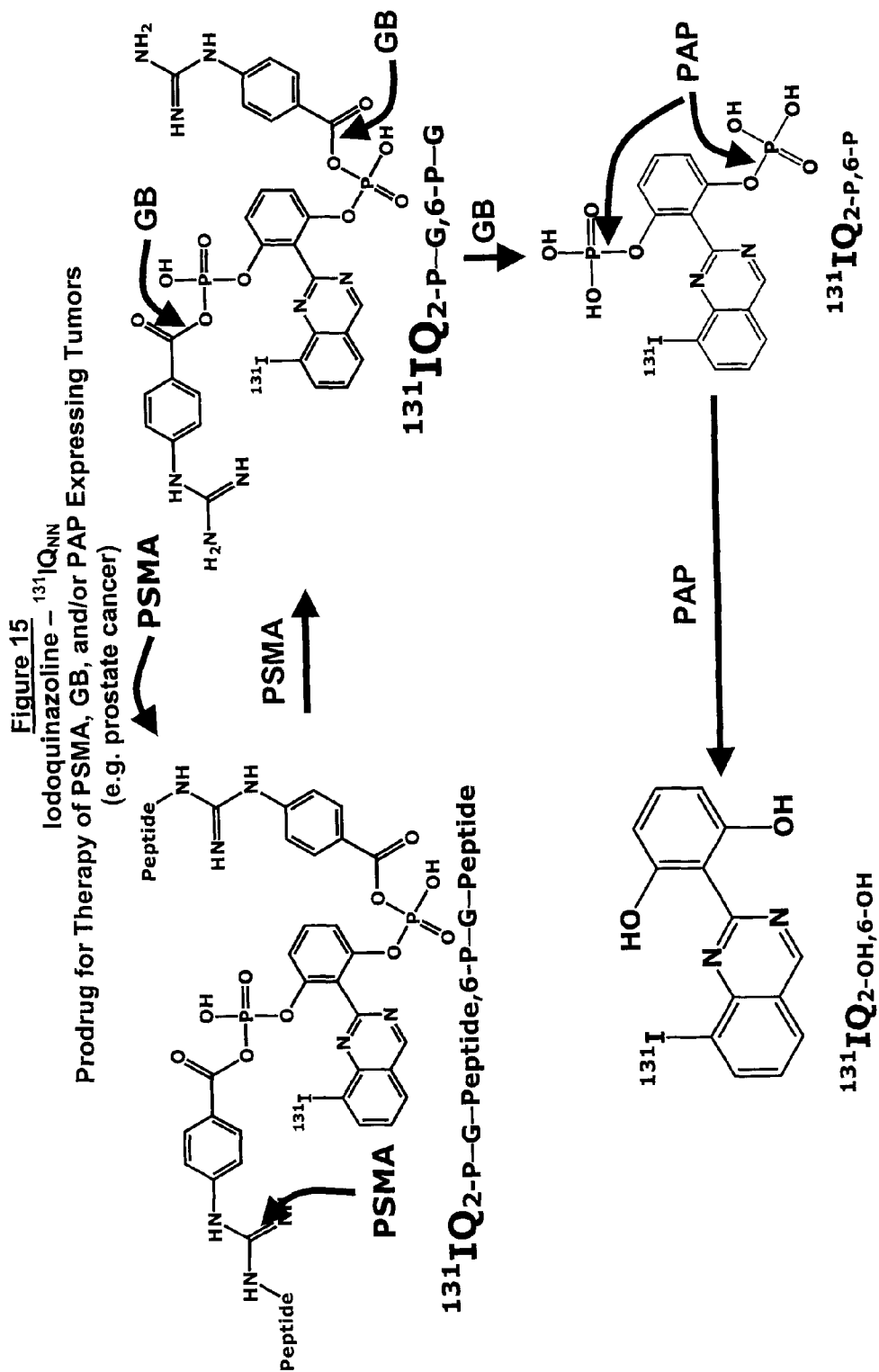
FIG. 15 is a scheme showing one embodiment of a compound of the invention. $^{131}I$=iodine-131; PSMA=prostate specific membrane antigen; G=guanidinobenzoate; GB=guanidinobenzoatase; PAP=prostatic acid phosphatase.
Figure 16:
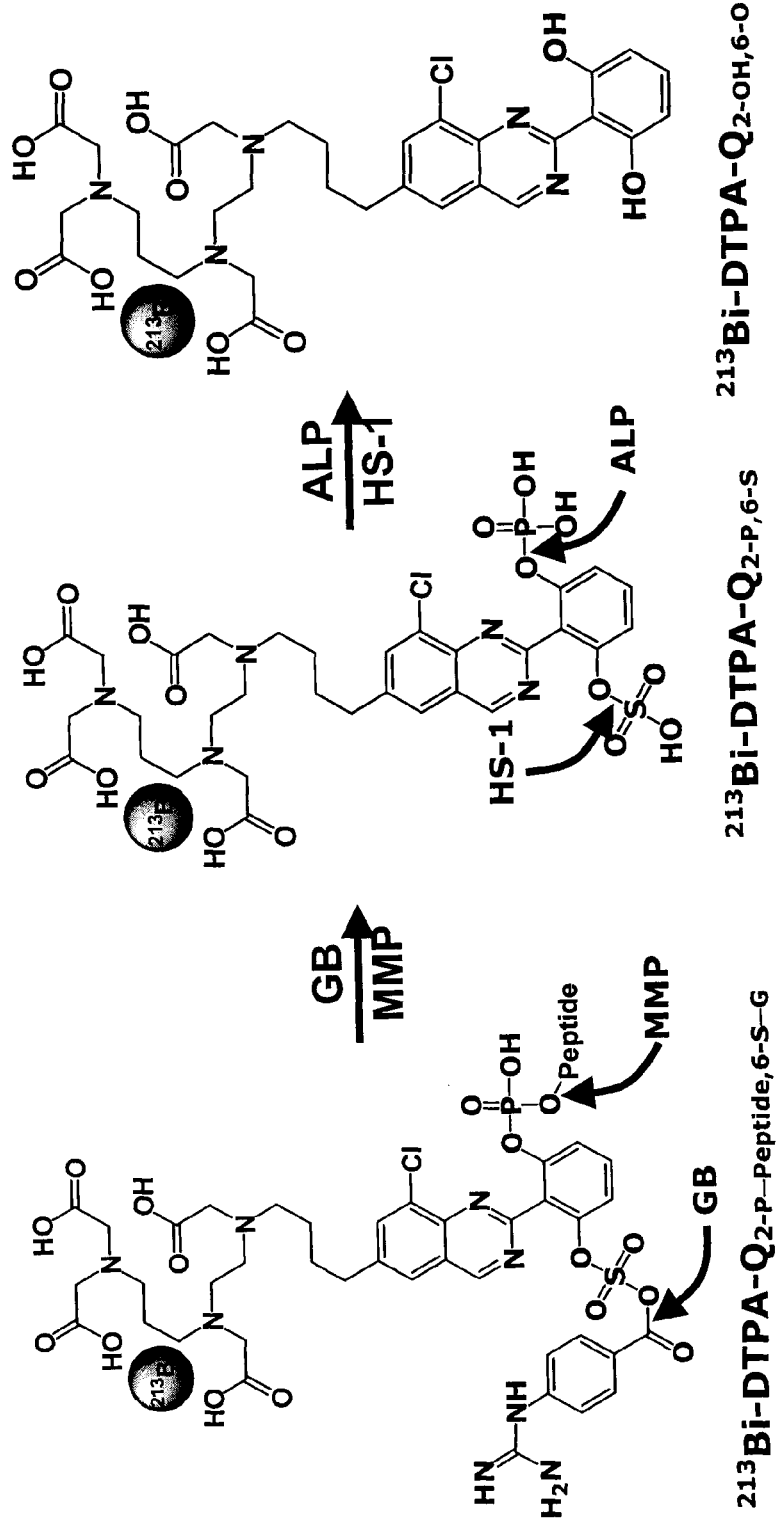
FIG. 16 is a scheme showing one embodiment of a compound of the invention. $^{213}Bi$=bismuth-213; DTPA=diethylene triamine pentaacetic acid; MMP=matrix metalloproteinase; G=guanidinobenzoate; GB=guanidinobenzoatase; ALP=alkaline phosphatase; HS-1=human sulfatase-1.
Figure 17:
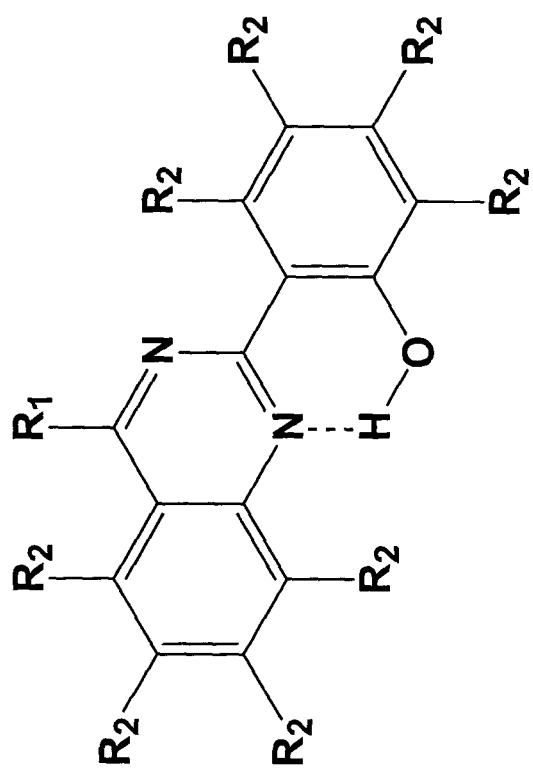
FIG. 17 is a structure of a compound according to certain embodiments of the invention, showing intramolecular hydrogen bond formation.
Figure 18:
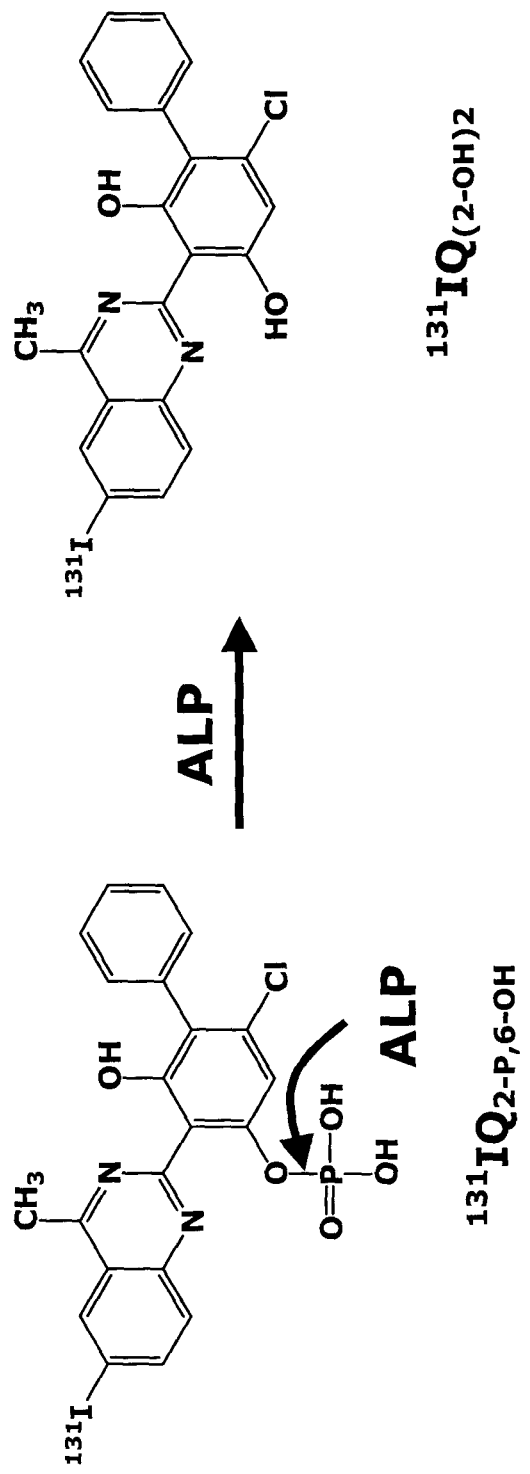
FIG. 18 is a scheme showing one embodiment of a compound of the invention. [131]I=iodine-131; ALP=alkaline phosphatase.
Figure 19:
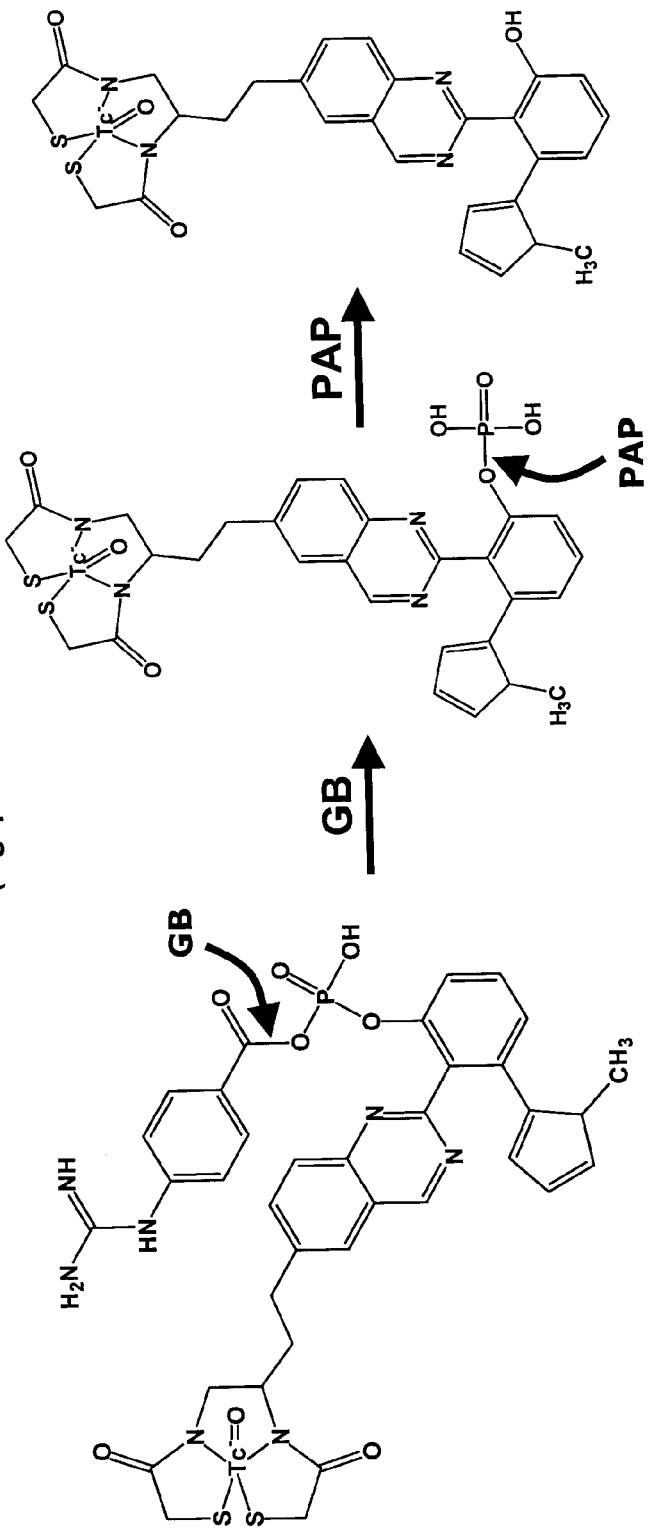
FIG. 19 is a scheme showing one embodiment of a compound of the invention. [99m]Tc=technetium-99m; DADT=diamide dithiolate; G=guanidinobenzoate; GB=guanidinobenzoatase; PAP=prostatic acid phosphatase.
Figure 20:
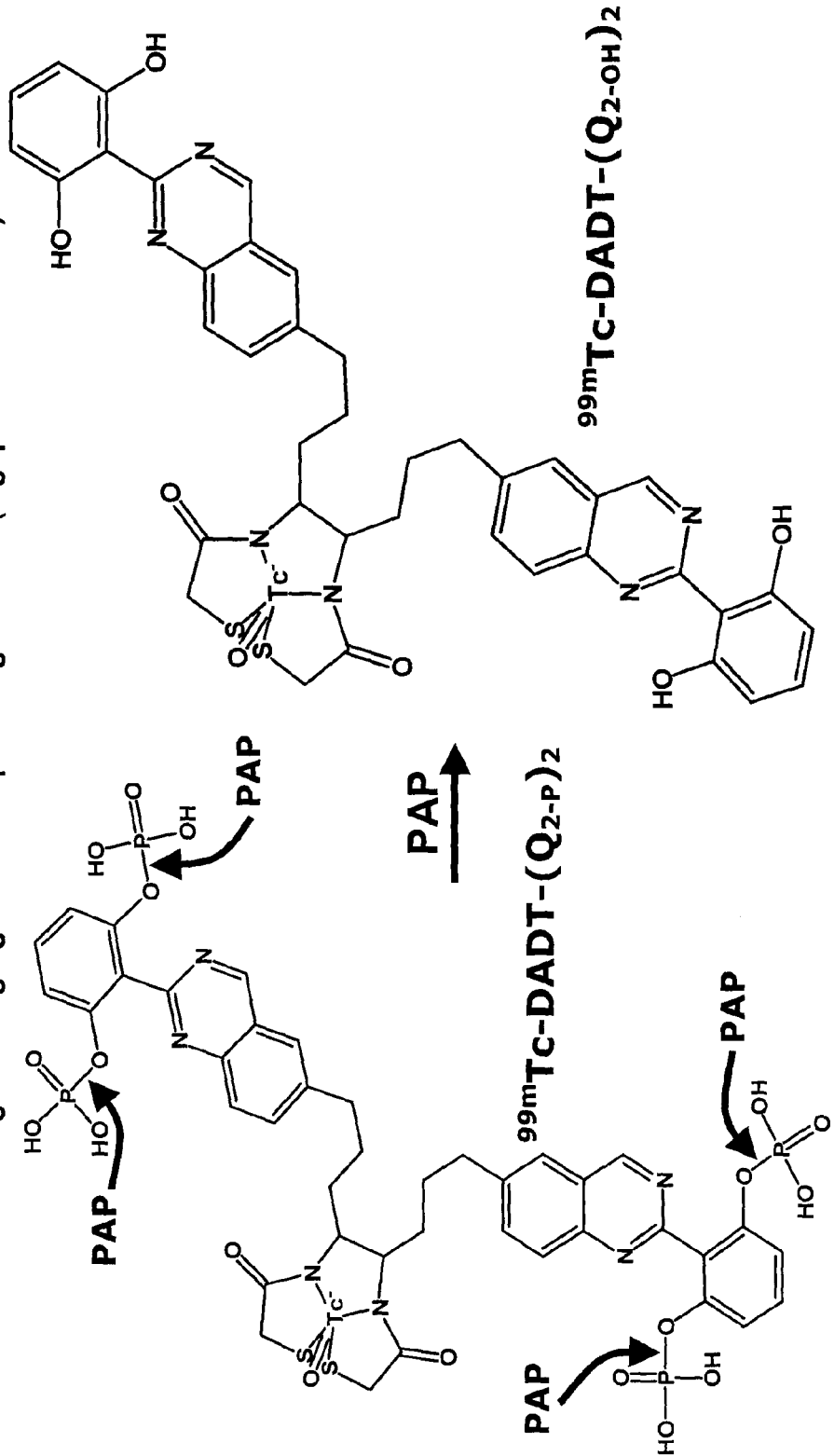
FIG. 20 is a scheme showing one embodiment of a compound of the invention. [99m]Tc=technetium-99m; DADT=diamide dithiolate; PAP=prostatic acid phosphatase.
Figure 21:
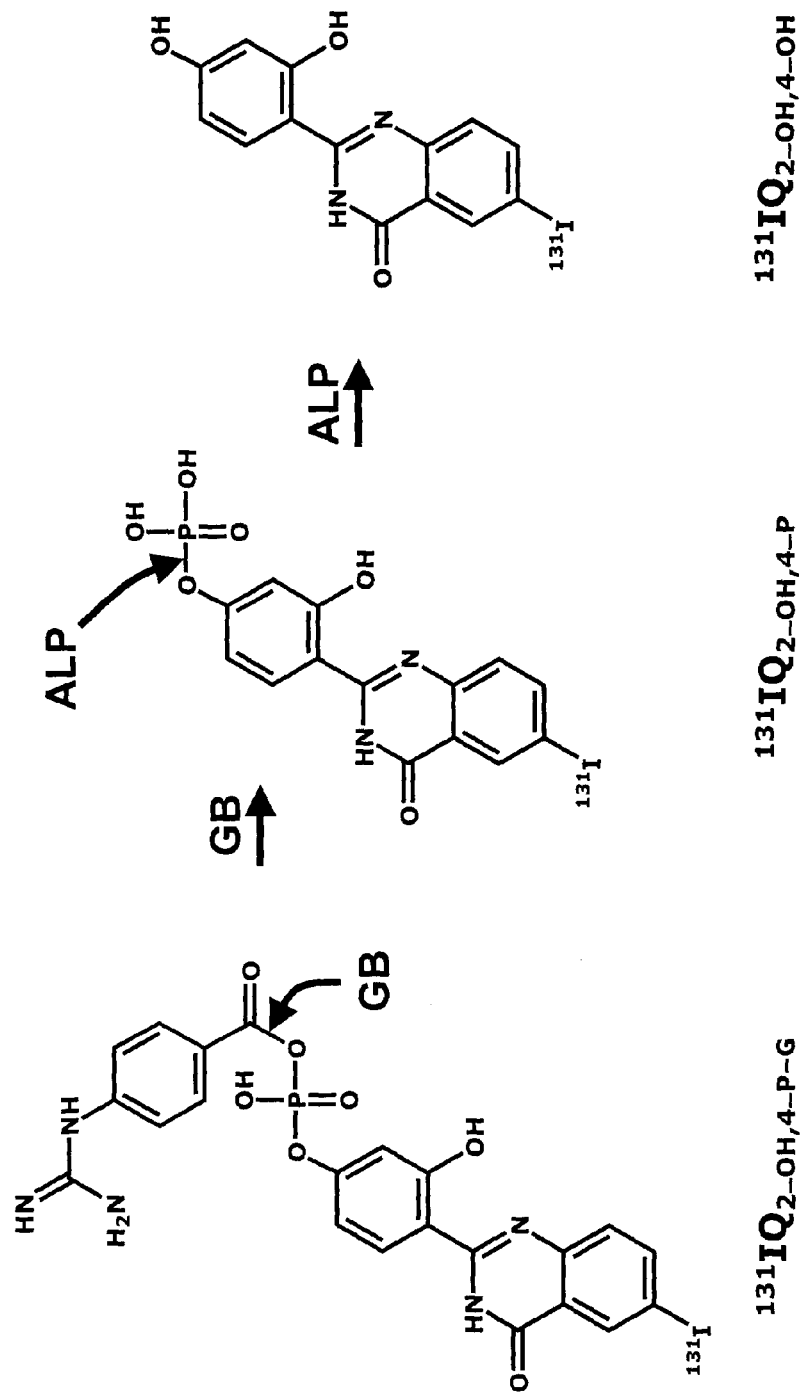
FIG. 21 is a scheme showing one embodiment of a compound of the invention. [131]I=iodine-131; GB=guanidinobenzoatase; ALP=alkaline phosphatase.
Figure 22:
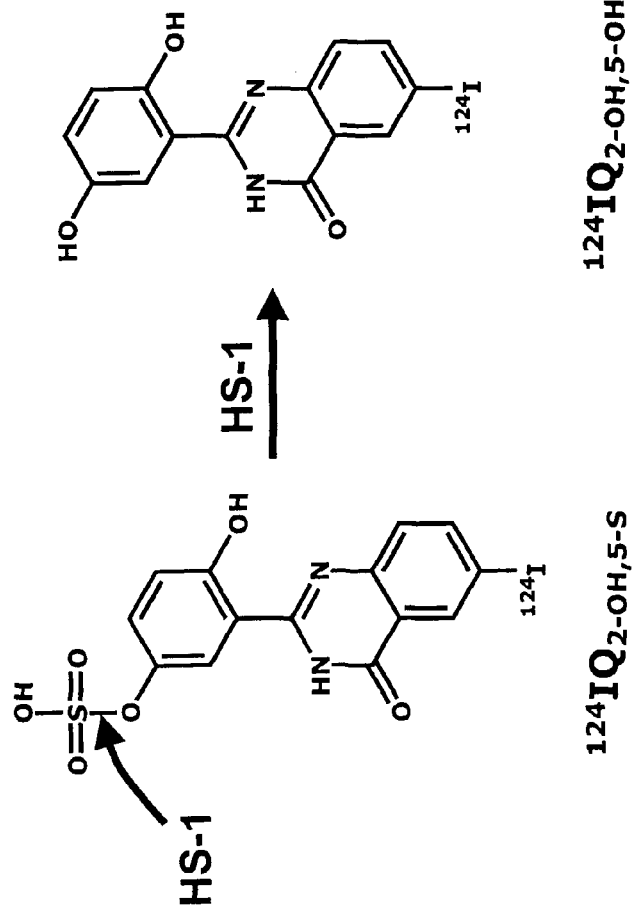
FIG. 22 is a scheme showing one embodiment of a compound of the invention. [124]I=iodine-124; HS-1=human sulfatase-1.
Figure 23:
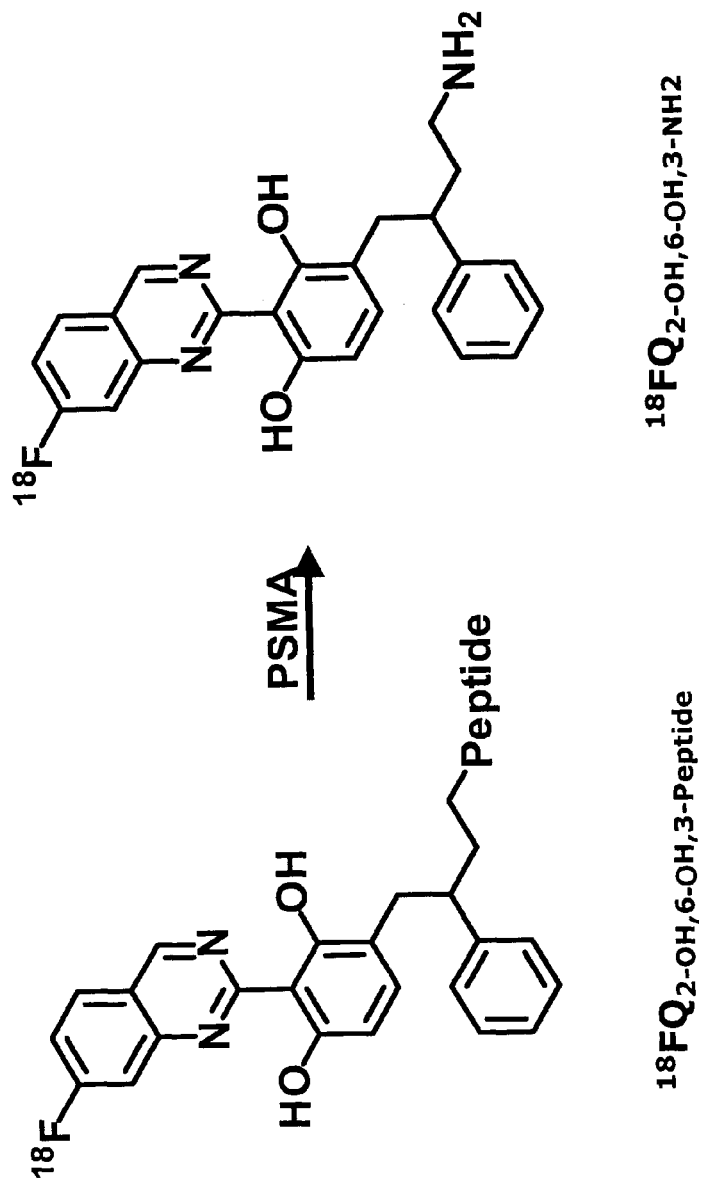
FIG. 23 is a scheme showing one embodiment of a compound of the invention. [18]F=fluorine-18; PSMA=prostate specific membrane antigen.
Figure 24:
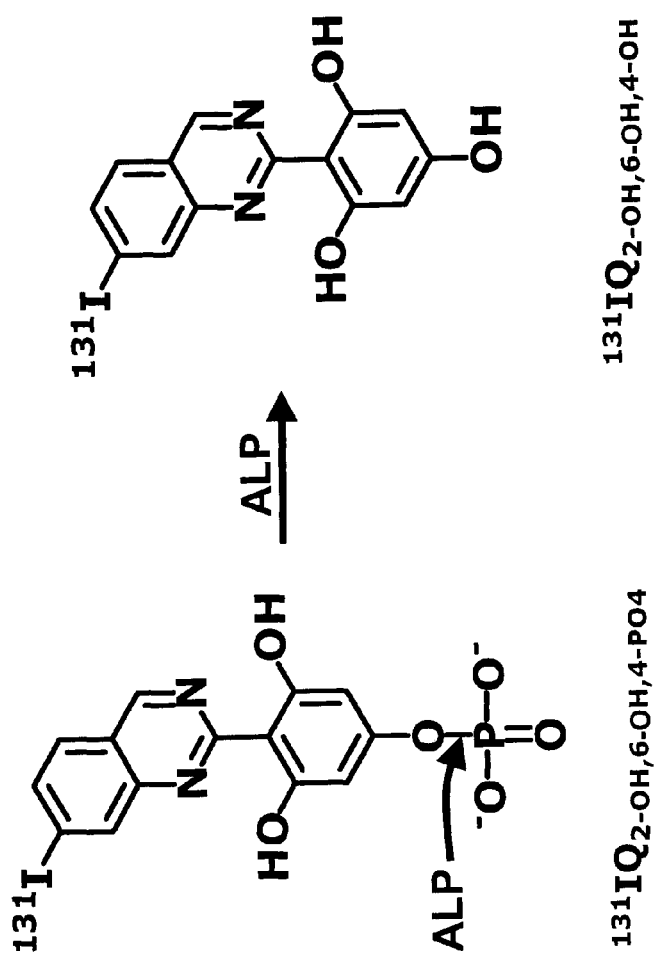
FIG. 24 is a scheme showing one embodiment of a compound of the invention. [131]I=iodine-131; ALP=alkaline phosphatase.

(XXX)

are particularly insoluble due to the formation of ring-like structures through intramolecular hydrogen bonding (i.e., between the nitrogen atom(s) of the quinazoline or quinazolinone ring and the phenolic hydroxyl groups, as shown in FIGS. 1, 10, and 17). As a result of the water-solubility of the pro-drug form (FIGS. 2-9, 11-16, and 18-20) and the insolubility of the cleaved form of the compounds, the compounds can be efficiently and selectively accumulated by tumor tissue.

Definitions

As used herein, the term "alkyl" refers to a straight chain, branched chain or cyclic saturated aliphatic hydrocarbon. An alkyl group may be bonded to an atom within a molecule of interest via any chemically suitable portion. Alkyl groups include groups having from 1 to 8 carbon atoms ($C_1$-$C_8$alkyl), from 1 to 6 carbon atoms ($C_1$-$C_6$alkyl) and from 1 to 4 carbon atoms ($C_1$-$C_4$alkyl), such as methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, cyclopropyl, cyclopropylmethyl, cyclopentyl, cyclopentylmethyl, cyclohexyl, cycloheptyl and norbornyl. An alkyl group may be optionally substituted as described herein.

Similarly, "alkenyl" refers to straight or branched chain alkene groups or cycloalkene groups. Within an alkenyl group, one or more unsaturated carbon-carbon double bonds are present. Alkenyl groups include $C_2$-$C_8$alkenyl, $C_2$-$C_6$alkenyl and $C_2$-$C_4$alkenyl groups, which have from 2 to 8, 2 to 6 or 2 to 4 carbon atoms, respectively, such as ethenyl, allyl or isopropenyl. "Alkynyl" refers to straight or branched chain alkyne groups, which have, one or more unsaturated carbon-carbon bonds, at least one of which is a triple bond. Alkynyl groups include $C_2$-$C_8$alkynyl, $C_2$-$C_6$alkynyl and $C_2$-$C_4$alkynyl groups, which have from 2 to 8, 2 to 6 or 2 to 4 carbon atoms, respectively. An alkenyl or alkynyl group may be optionally substituted as described herein.

By "alkoxy," as used herein, is meant an alkyl, alkenyl or alkynyl group as described above attached via an oxygen bridge. Alkoxy groups include $C_1$-$C_8$alkoxy, $C_1$-$C_6$alkoxy and $C_1$-$C_4$alkoxy groups, which have from 1 to 8, 1 to 6 or 1 to 4 carbon atoms, respectively. Alkoxy groups include, for example, methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy. An alkoxy group may be optionally substituted as described herein.

"Alkylamino" refers to a secondary or tertiary amine having the general structure —NH-alkyl or —N(alkyl)(alkyl), wherein each alkyl may be the same or different. Such groups include, for example, mono- and di-($C_1$-$C_8$alkyl)amino groups, in which each alkyl may be the same or different and may contain from 1 to 8 carbon atoms, as well as mono- and di-($C_1$-$C_6$alkyl)amino groups and mono- and di-($C_1$-$C_4$alkyl) amino groups. Alkylaminoalkyl refers to an alkylamino group linked via an alkyl group (i.e., a group having the general structure -alkyl-NH-alkyl or -alkyl-N(alkyl)(alkyl)). Such groups include, for example, mono- and di-($C_1$-$C_8$alkyl)amino$C_1$-$C_8$alkyl, mono- and di-($C_1$-$C_6$alkyl)amino$C_1$-$C_6$alkyl and mono- and di-($C_1$-$C_4$alkyl)amino$C_1$-$C_4$alkyl, in which each alkyl may be the same or different.

An "aryl" group is an aromatic 5-10 membered ring which may be carbocyclic (e.g., phenyl) or heterocyclic (e.g., pyridyl, thiophenyl, furanyl) and may be optionally substituted as described herein. An aryl group may include fused rings which can be aromatic (e.g., naphthyl, quinolinyl) or nonaromatic (e.g., tetrahydronaphthyl).

The term "halogen" includes all the isotopes of fluorine, chlorine, bromine, iodine, and astatine.

A "substituent," as used herein, refers to a molecular moiety that is covalently bonded to an atom within a molecule of interest. For example, a "ring substituent" may be a moiety such as a halogen, alkyl group, haloalkyl group or other group discussed herein that is covalently bonded to an atom (preferably a carbon or nitrogen atom) that is a ring member. The term "substitution" refers to replacing a hydrogen atom in a molecular structure with a substituent as described above, such that the valence on the designated atom is not exceeded, and such that a chemically stable compound (i.e., a compound that can be isolated, characterized, and tested for biological activity) results from the substitution.

Groups that are "optionally substituted" are unsubstituted or are substituted by other than hydrogen at one or more available positions, typically 1, 2, 3, 4 or 5 positions, by one or more suitable groups (which may be the same or different). Such optional substituents include, for example, hydroxy, halogen, cyano, nitro, $C_1$-$C_8$alkyl, $C_2$-$C_8$alkenyl, $C_2$-$C_8$alkynyl, $C_1$-$C_8$alkoxy, $C_1$-$C_8$alkylthio, amino, mono- or di-($C_1$-$C_8$alkyl)amino, —COOH, —CONH$_2$, —SO$_2$NH$_2$, and/or mono or di($C_1$-$C_8$alkyl)sulfonamido, as well as carbocyclic and heterocyclic groups. Certain optionally substituted groups are substituted with from 0 to 3 independently selected substituents.

A moiety capable of complexing with a radionuclide includes metal-chelating moieties such as diamino-dithiolate ligands, amino-amido-dithiolate ligands, and ligands such as diethylenetriaminepentaacetic acid (DTPA), diaminedithiol (DADT) ligands, 1,4,7,10-tetraazacyclotetradecane-1,4,7,10-tetraacetic acid (DOTA) and derivatives thereof, and the like. In general, a chelating moiety should be physiologically compatible (e.g., substantially non-toxic) and should not interfere with the physiological properties of the compound of the invention such as solubility, metabolism, distribution, and the like.

The term "subject" or "patient" refers to an organism, e.g., a mammal, which is capable of suffering from or afflicted with a solid tumor. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from, a solid tumor.

Compounds

In another aspect, the invention provides a compound or salt represented by the formula:

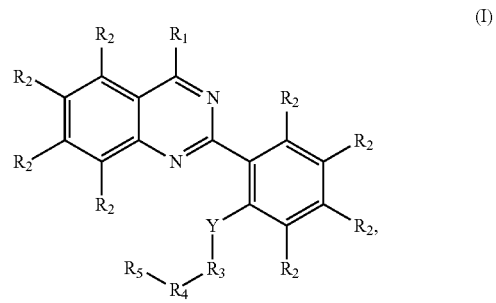

(I)

in which $R_1$ is H, COOH, amino, mono- or di($C_1$-$C_6$alkyl)amino, $C_1$-$C_8$alkyl, $C_2$-$C_8$alkenyl, $C_2$-$C_8$alkynyl, $C_3$-$C_8$cycloalkyl, aryl, halogen, $C_1$-$C_8$alkoxy, nitro, or cyano; or $R_1$ is a radionuclide or a moiety containing, or capable of complexing with, a radionuclide;

$R_2$ is, independently for each occurrence, H, hydroxy, COOH, amino, mono- or di($C_1$-$C_6$alkyl)amino, $C_1$-$C_8$alkyl, $C_2$-$C_8$alkenyl, $C_2$-$C_8$alkynyl, $C_3$-$C_8$cycloalkyl, aryl, halogen, $C_1$-$C_8$alkoxy, nitro, cyano, or a radionuclide or a moiety containing, or capable of complexing with, a radionuclide;

$R_3$ and $R_4$ are each independently a direct bond or a group which can be cleaved by an enzyme, provided that at least one of $R_3$ and $R_4$ is a group which can be cleaved by an enzyme;

$R_5$ is a group which can be cleaved by an enzyme; and

Y is O, S or NH or N(alkyl) (e.g., NCH$_3$);

provided that at least one occurrence of $R_1$ or $R_2$ is a radionuclide or a moiety containing, or capable of complexing with, a radionuclide;

or a pharmaceutically acceptable salt thereof.

In certain embodiments, $R_3$ and $R_4$ are each independently a group which can be cleaved by an enzyme.

In certain embodiments, the compound or salt can be represented by the formula:

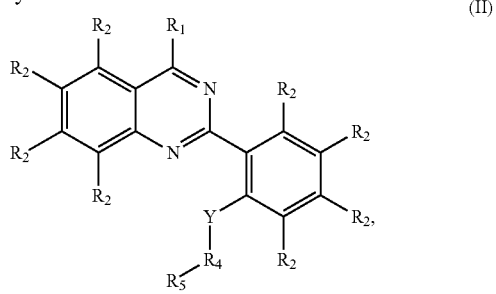

(II)

in which Y, $R_1$, $R_2$, $R_4$, and $R_5$ are as defined for Formula I.

In certain embodiments, the compound or salt can be represented by the formula:

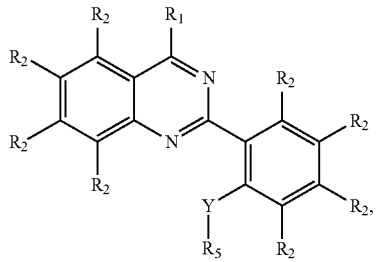

(III)

in which Y, $R_1$, $R_2$, and $R_5$ are as defined for Formula I.

In certain embodiments, the compound or salt can be represented by the formula:

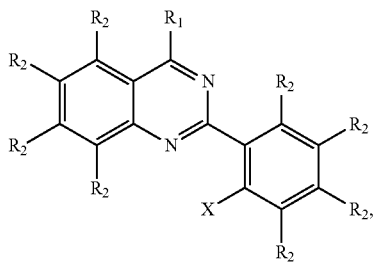

(IV)

in which $R_1$ and $R_2$ are as defined for Formula I; and

X is OH, SH or $NH_2$ or NH(alkyl) (e.g., $NHCH_3$).

In another aspect, the invention provides a compound or salt represented by the formula:

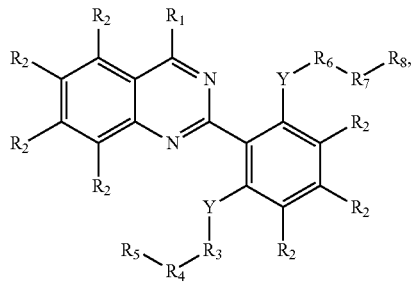

(V)

in which $R_1$ is H, COOH, amino, mono- or di($C_1$-$C_6$alkyl)amino, halogen, $C_1$-$C_8$alkyl, $C_2$-$C_8$alkenyl, $C_2$-$C_8$alkynyl, $C_3$-$C_8$cycloalkyl, aryl, $C_1$-$C_8$alkoxy, nitro, or cyano; or $R_1$ is a radionuclide or a moiety containing, or capable of complexing with, a radionuclide;

$R_2$ is, independently for each occurrence, H, hydroxy, COOH, amino, mono- or di($C_1$-$C_6$alkyl)amino, $C_1$-$C_8$alkyl, $C_2$-$C_8$alkenyl, $C_2$-$C_8$alkynyl, $C_3$-$C_8$cycloalkyl, aryl, halogen, $C_1$-$C_8$alkoxy, nitro, cyano, or a radionuclide or a moiety containing, or capable of complexing with, a radionuclide;

$R_3$, $R_4$, $R_6$ and $R_7$ are each independently a direct bond or a group which can be cleaved by an enzyme;

$R_5$ and $R_8$ are each independently a group which can be cleaved by an enzyme; and Y is, independently for each occurrence, O, S or NH or N(alkyl) (e.g., $NCH_3$);

provided that at least one occurrence of $R_1$ or $R_2$ is a radionuclide or a moiety containing, or capable of complexing with, a radionuclide;

or a pharmaceutically acceptable salt thereof.

In certain embodiments, $R_3$ and $R_4$ are each independently a group which can be cleaved by an enzyme. In certain embodiments, $R_6$ and $R_7$ are each independently a group which can be cleaved by an enzyme. In certain embodiments, $R_3$ and $R_6$ are each independently a group which can be cleaved by an enzyme. In certain embodiments, $R_5$ and $R_8$ are identical enzyme cleavable moieties or different enzyme-cleavable moieties which are cleaved by a first selected enzyme, $R_3$ and $R_6$ are identical enzyme cleavable moieties or different enzyme-cleavable moieties which are cleaved by a second selected enzyme, and $R_4$ and $R_7$ are identical enzyme cleavable moieties or different enzyme-cleavable moieties which are cleaved by a third selected enzyme. In certain embodiments, $R_5$ and $R_8$ are independently selected enzyme cleavable moieties which are respectively cleaved by a first enzyme and a second enzyme, $R_3$ and $R_6$ are independently selected enzyme cleavable moieties which are respectively cleaved by a third enzyme and a fourth enzyme, and $R_4$ and $R_7$ are independently selected enzyme cleavable moieties which are respectively cleaved by a fifth enzyme and a sixth enzyme.

In certain embodiments, the compound or salt can be represented by the formula:

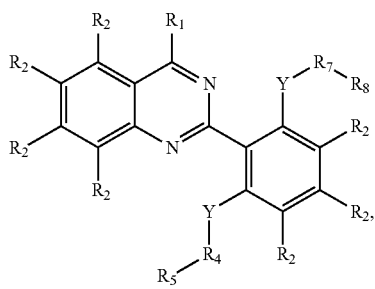

(VI)

in which Y, $R_1$, $R_2$, $R_4$, $R_5$, $R_7$, and $R_8$ are as defined for Formula V, provided that at least one occurrence of $R_1$ or $R_2$ is a radionuclide or a moiety containing, or capable of complexing with, a radionuclide. In certain embodiments, $R_5$ and $R_8$ are identical enzyme cleavable moieties or different enzyme-cleavable moieties which are cleaved by a first selected enzyme, and $R_3$ and $R_6$ are identical enzyme cleavable moieties or different enzyme-cleavable moieties which are cleaved by a second selected enzyme. In certain embodiments, $R_5$ and $R_8$ are independently selected enzyme cleavable moieties which are respectively cleaved by a first enzyme and a second enzyme, and $R_3$ and $R_6$ are independently selected enzyme cleavable moieties which are respectively cleaved by a third enzyme and a fourth enzyme.

In certain embodiments, the compound or salt can be represented by the formula:

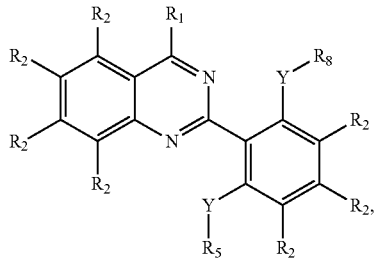

(VII)

in which Y, $R_1$, $R_2$, $R_5$, and $R_8$ are as defined for Formula V, provided that at least one occurrence of $R_1$ or $R_2$ is a radionuclide or a moiety containing, or capable of complexing with, a radionuclide. In certain embodiments, $R_5$ and $R_8$ are the same enzyme cleavable moiety or any different enzyme-cleavable moieties which are cleaved by the same enzyme. In certain embodiments, $R_5$ and $R_8$ are the different enzyme cleavable moieties which are cleaved by different enzymes.

In certain embodiments, the compound or salt can be represented by the formula:

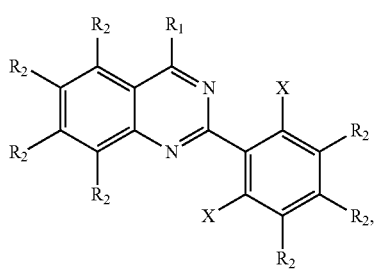

(VIII)

in which $R_1$ and $R_2$ are as defined for Formula V, provided that at least one occurrence of $R_1$ or $R_2$ is a radionuclide or a moiety containing, or capable of complexing with, a radionuclide; and X is OH, SH or $NH_2$ or NH(alkyl) (e.g., $NHCH_3$).

In another aspect, the invention provides a compound or salt represented by the formula:

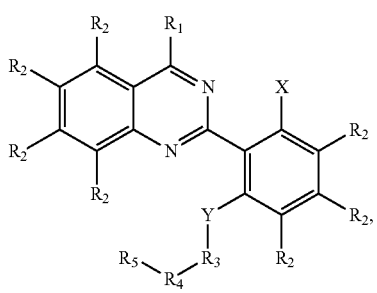

(IX)

in which $R_1$ is H, COOH, amino, mono- or di($C_1$-$C_6$alkyl)amino, $C_1$-$C_8$alkyl, $C_2$-$C_8$alkenyl, $C_2$-$C_8$alkynyl, $C_3$-$C_8$cycloalkyl, aryl, halogen, $C_1$-$C_8$alkoxy, nitro, or cyano; or $R_1$ is a radionuclide or a moiety containing, or capable of complexing with, a radionuclide;

$R_2$ is, independently for each occurrence, H, hydroxy, COOH, amino, mono- or di($C_1$-$C_6$alkyl)amino, $C_1$-$C_8$alkyl, $C_2$-$C_8$alkenyl, $C_2$-$C_8$alkynyl, $C_3$-$C_8$cycloalkyl, aryl, halogen, $C_1$-$C_8$alkoxy, nitro, cyano, or a radionuclide or a moiety containing, or capable of complexing with, a radionuclide;

$R_3$ and $R_4$ are each independently a direct bond or a group which can be cleaved by an enzyme, provided that at least one of $R_3$ and $R_4$ is a group which can be cleaved by an enzyme;

$R_5$ is a group which can be cleaved by an enzyme;

Y is O, S or NH or N(alkyl) (e.g., $NCH_3$); and

X is OH, SH or $NH_2$ or NH(alkyl) (e.g., $NHCH_3$);

provided that at least one occurrence of $R_1$ or $R_2$ is a radionuclide or a moiety containing, or capable of complexing with, a radionuclide;

or a pharmaceutically acceptable salt thereof.

In certain embodiments, $R_3$ and $R_4$ are each independently a group which can be cleaved by an enzyme.

In certain embodiments, the compound or salt can be represented by the formula:

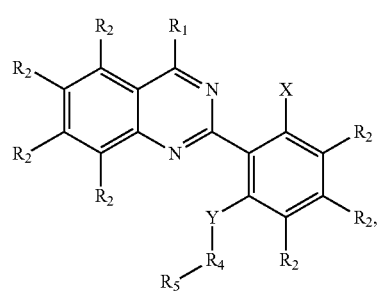

(X)

in which Y, $R_1$, $R_2$, $R_4$, and $R_5$ are as defined for Formula IX, provided that at least one occurrence of $R_1$ or $R_2$ is a radionuclide or a moiety containing, or capable of complexing with, a radionuclide; and X is OH, SH or $NH_2$ or NH(alkyl) (e.g., $NHCH_3$).

In certain embodiments, the compound or salt can be represented by the formula:

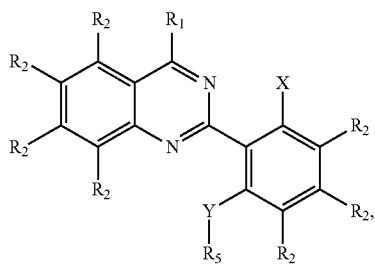

(XI)

in which Y, $R_1$, $R_2$, and $R_5$ are as defined for Formula IX, provided that at least one occurrence of $R_1$ or $R_2$ is a radionuclide or a moiety containing, or capable of complexing with, a radionuclide; and X is OH, SH or $NH_2$ or NH(alkyl) (e.g., $NHCH_3$).

In another aspect, the invention provides a compound or salt represented by the formula:

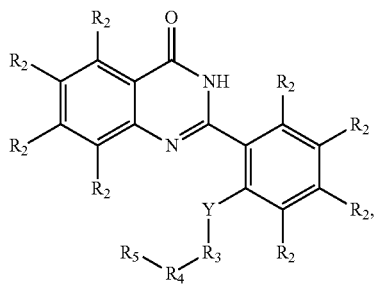

(XII)

in which
R$_2$ is, independently for each occurrence, H, hydroxy, COOH, amino, mono- or di(C$_1$-C$_6$alkyl)amino, C$_1$-C$_8$alkyl, C$_2$-C$_8$alkenyl, C$_2$-C$_8$alkynyl, C$_3$-C$_8$cycloalkyl, aryl, halogen, C$_1$-C$_8$alkoxy, nitro, cyano, or a radionuclide or a moiety containing, or capable of complexing with, a radionuclide;

R$_3$ and R$_4$ are each independently a direct bond or a group which can be cleaved by an enzyme, provided that at least one of R$_3$ and R$_4$ is a group which can be cleaved by an enzyme;

R$_5$ is a group which can be cleaved by an enzyme; and

Y is O, S or NH or N(alkyl) (e.g., NCH$_3$);

provided that at least one occurrence of R$_2$ is a radionuclide or a moiety containing, or capable of complexing with, a radionuclide;

or a pharmaceutically acceptable salt thereof.

In certain embodiments, R$_3$ and R$_4$ are each independently a group which can be cleaved by an enzyme.

In certain embodiments, the compound or salt can be represented by the formula:

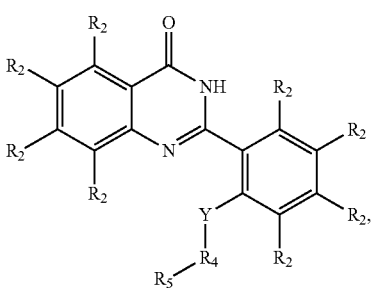

(XIII)

in which Y, R$_2$, R$_4$, and R$_5$ are as defined for Formula XII, provided that at least one occurrence of R$_2$ is a radionuclide or a moiety containing, or capable of complexing with, a radionuclide.

In certain embodiments, the compound or salt can be represented by the formula:

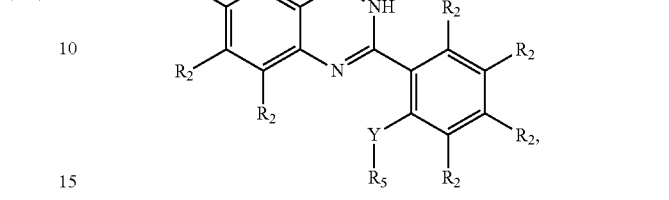

(XIV)

in which Y, R$_2$, and R$_5$ are as defined for Formula XII, provided that at least one occurrence of R$_1$ or R$_2$ is a radionuclide or a moiety containing, or capable of complexing with, a radionuclide.

In certain embodiments, the compound or salt can be represented by the formula:

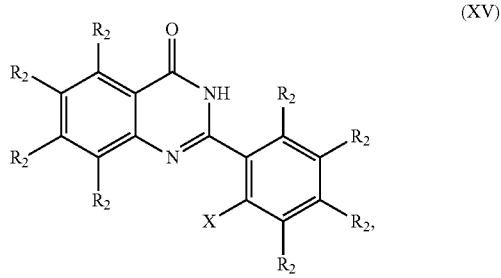

(XV)

in which R$_2$ is as defined for Formula XII, provided that at least one occurrence of R$_1$ or R$_2$ is a radionuclide or a moiety containing, or capable of complexing with, a radionuclide; and X is OH, SH or NH$_2$ or NH(alkyl) (e.g., NHCH$_3$).

In another aspect, the invention provides a compound or salt represented by the formula:

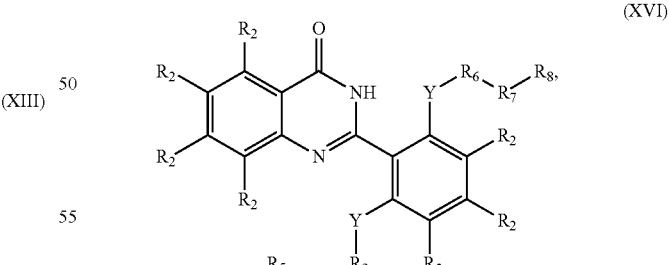

(XVI)

in which
R$_2$ is, independently for each occurrence, H, hydroxy, COOH, amino, mono- or di(C$_1$-C$_6$alkyl)amino, C$_1$-C$_8$alkyl, C$_2$-C$_8$alkenyl, C$_2$-C$_8$alkynyl, C$_3$-C$_8$cycloalkyl, aryl, halogen, C$_1$-C$_8$alkoxy, nitro, cyano, or a radionuclide or a moiety containing, or capable of complexing with, a radionuclide;

$R_3$, $R_4$, $R_6$ and $R_7$ are each independently a direct bond or a group which can be cleaved by an enzyme;

$R_5$ and $R_8$ are each independently a group which can be cleaved by an enzyme; and Y is, independently for each occurrence, O, S or NH or N(alkyl) (e.g., $NCH_3$);

provided that at least one occurrence of $R_2$ is a radionuclide or a moiety containing, or capable of complexing with, a radionuclide;

or a pharmaceutically acceptable salt thereof.

In certain embodiments, $R_3$ and $R_4$ are each independently a group which can be cleaved by an enzyme. In certain embodiments, $R_6$ and $R_7$ are each independently a group which can be cleaved by an enzyme. In certain embodiments, $R_3$ and $R_6$ are each independently a group which can be cleaved by an enzyme. In certain embodiments, $R_5$ and $R_8$ are identical enzyme cleavable moieties or different enzyme-cleavable moieties which are cleaved by a first selected enzyme, $R_3$ and $R_6$ are identical enzyme cleavable moieties or different enzyme-cleavable moieties which are cleaved by a second selected enzyme, and $R_4$ and $R_7$ are identical enzyme cleavable moieties or different enzyme-cleavable moieties which are cleaved by a third selected enzyme. In certain embodiments, $R_5$ and $R_8$ are independently selected enzyme cleavable moieties which are respectively cleaved by a first enzyme and a second enzyme, $R_3$ and $R_6$ are independently selected enzyme cleavable moieties which are respectively cleaved by a third enzyme and a fourth enzyme, and $R_4$ and $R_7$ are independently selected enzyme cleavable moieties which are respectively cleaved by a fifth enzyme and a sixth enzyme.

In certain embodiments, the compound or salt can be represented by the formula:

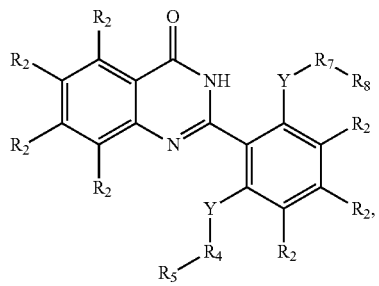

(XVII)

in which Y, $R_2$, $R_4$, $R_5$, $R_7$, and $R_8$ are as defined for Formula XVI, provided that at least one occurrence of $R_2$ is a radionuclide or a moiety containing, or capable of complexing with, a radionuclide. In certain embodiments, $R_5$ and $R_8$ are identical enzyme cleavable moieties or different enzyme-cleavable moieties which are cleaved by a first selected enzyme, and $R_3$ and $R_6$ are identical enzyme cleavable moieties or different enzyme-cleavable moieties which are cleaved by a second selected enzyme. In certain embodiments, $R_5$ and $R_8$ are independently selected enzyme cleavable moieties which are respectively cleaved by a first enzyme and a second enzyme, and $R_3$ and $R_6$ are independently selected enzyme cleavable moieties which are respectively cleaved by a third enzyme and a fourth enzyme.

In certain embodiments, the compound or salt can be represented by the formula:

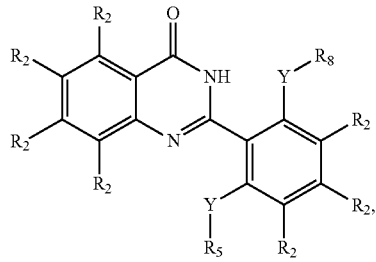

(XVIII)

in which Y, $R_2$, $R_5$, and $R_8$ are as defined for Formula XVI, provided that at least one occurrence of $R_2$ is a radionuclide or a moiety containing, or capable of complexing with, a radionuclide. In certain embodiments, $R_5$ and $R_8$ are the same enzyme cleavable moiety or any different enzyme-cleavable moieties which are cleaved by the same enzyme. In certain embodiments, $R_5$ and $R_8$ are the different enzyme cleavable moieties which are cleaved by different enzymes.

In certain embodiments, the compound or salt can be represented by the formula:

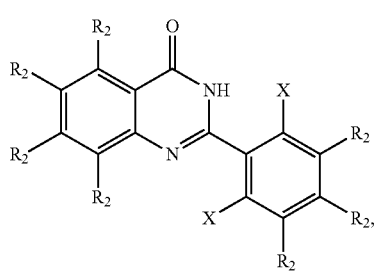

(XIX)

in which $R_2$ is as defined for Formula XVI, provided that at least one occurrence of $R_2$ is a radionuclide or a moiety containing, or capable of complexing with, a radionuclide; and X is OH, SH or $NH_2$ or NH(alkyl) (e.g., $NHCH_3$).

In another aspect, the invention provides a compound or salt represented by the formula:

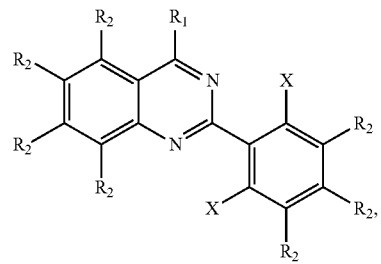

(XX)

in which

X, $R_1$ and $R_2$ have the meanings of the corresponding variable groups of Formula V, provided that at least one occurrence of $R_1$ or $R_2$ is a radionuclide or a moiety containing, or capable of complexing with, a radionuclide;

or $R_2$ is independently for each occurrence $R_3$—$R_4$—$R_5$, $R_4$—$R_5$, or $R_5$, or —Y—$R_3$—$R_4$—$R_5$, —Y—$R_4$—$R_5$, or —Y—$R_5$ as defined for Formula V; and at least one $R_2$ is $R_3$—$R_4$—$R_5$, $R_4$—$R_5$, or $R_5$ as defined for Formula V.

In another aspect, the invention provides a compound or salt represented by the formula:

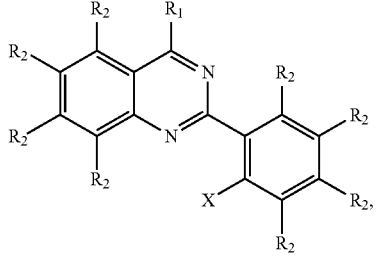

(XXI)

in which $X$, $R_1$ and $R_2$ have the meanings of the corresponding variable groups of Formula I, provided that at least one occurrence of $R_1$ or $R_2$ is a radionuclide or a moiety containing, or capable of complexing with, a radionuclide; or $R_2$ is independently for each occurrence $R_3$—$R_4$—$R_5$, $R_4$—$R_5$, or $R_5$, or —Y—$R_3$—$R_4$—$R_5$, —Y—$R_4$—$R_5$, or —Y—$R_5$ as defined for Formula I; and at least one $R_2$ is $R_3$—$R_4$—$R_5$, $R_4$—$R_5$, or $R_5$ as defined for Formula I.

In another aspect, the invention provides a compound or salt represented by the formula:

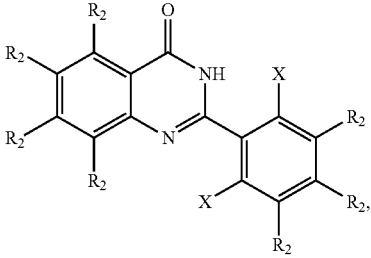

(XXII)

in which $X$ and $R_2$ have the meanings of the corresponding variable groups of Formula XII, provided that at least one occurrence of $R_2$ is a radionuclide or a moiety containing, or capable of complexing with, a radionuclide; or $R_2$ is independently for each occurrence $R_3$—$R_4$—$R_5$, $R_4$—$R_5$, or $R_5$ as defined for Formula XII; and at least one $R_2$ is $R_3$—$R_4$—$R_5$, $R_4$—$R_5$, or $R_5$ as defined for Formula XII.

In another aspect, the invention provides a compound or salt represented by the formula:

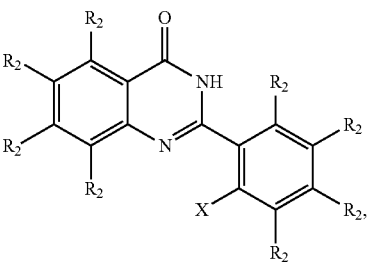

(XXIII)

in which $X$ and $R_2$ have the meanings of the corresponding variable groups of Formula XII, provided that at least one occurrence of $R_2$ is a radionuclide or a moiety containing, or capable of complexing with, a radionuclide; or $R_2$ is independently for each occurrence $R_3$—$R_4$—$R_5$, $R_4$—$R_5$, or $R_5$ as defined for Formula XII and at least one $R_2$ is $R_3$—$R_4$—$R_5$, $R_4$—$R_5$, or $R_5$ as defined for Formula XII.

In certain embodiments of a compound or salt of Formulae V and XVI, $R_3$, $R_4$, $R_6$, and $R_7$ are each a direct bond. In certain embodiments of Formulae V-VII and XVI-XVIII, at least one of $R_5$ and $R_8$ is a group which can be cleaved by an enzyme. In certain embodiments of Formulae V-VII and XVI-XVIII, one of $R_5$ and $R_8$ is H and the other is a group which can be cleaved by an enzyme. In certain embodiments, $R_5$ and $R_8$ are each a group which can be cleaved by an enzyme. In certain embodiments, $R_5$ and $R_8$ are different. In certain embodiments, $R_5$ and $R_8$ can be cleaved by the same enzyme. In certain embodiments, $R_5$ and $R_8$ are the same.

In certain embodiments of a compound or salt of Formulae V and XVI, $R_3$, $R_4$, $R_5$, and $R_6$ are each independently a direct bond. In certain embodiments, $R_3$, $R_4$, $R_5$, $R_6$, $R_7$, and $R_8$ are each a group which can be cleaved by an enzyme. In certain embodiments, one of $R_2$, $R_3$, $R_4$, $R_5$, $R_6$, and $R_7$ is a H and the others are each a group which can be cleaved by an enzyme. In certain embodiments, $R_5$ and $R_8$ are different and each can be cleaved by a different enzyme. In certain embodiments, $R_3$ and $R_6$ are different and each can be cleaved by a different enzyme. In certain embodiments, $R_4$ and $R_7$ are different and each can be cleaved by a different enzyme. In certain embodiments, $R_4$ and $R_7$ are the same and each can be cleaved by the same enzyme. In certain embodiments, $R_3$ and $R_6$ are the same and each can be cleaved by the same enzyme. In certain embodiments, $R_5$ and $R_8$ are the same and each can be cleaved by the same enzyme.

In certain embodiments, the compound or salt can be represented by the formula:

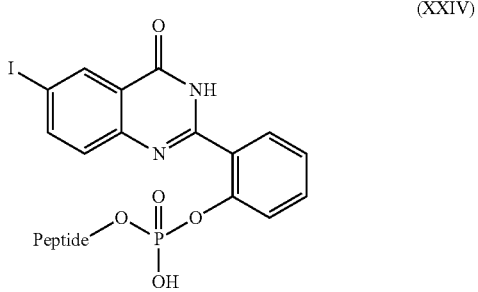

(XXIV)

wherein Peptide is a peptide or polypeptide chain having at least three amino acid residues and having a sequence that is cleavable by a peptidase or a proteinase. In preferred embodiments, the phosphate or phosphate ester is cleavable by a phosphatase after cleavage of the Peptide.

In another embodiment, the compound or salt can be represented by the formula:

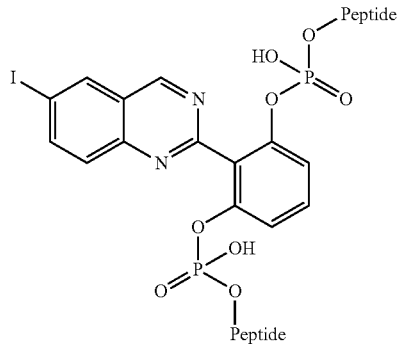
(XXV)

wherein Peptide is, independently for each occurrence, a peptide or polypeptide chain having at least three amino acid residues and having a sequence that is cleavable by a peptidase or a proteinase. In preferred embodiments of Formula XXV, the phosphate group is cleavable by a phosphatase after cleavage of the Peptide.

In another embodiment, the compound or salt can be represented by the formula:

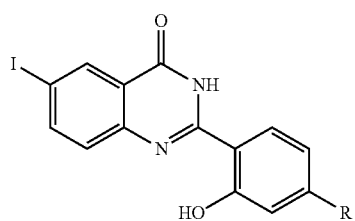
(XXVI)

wherein R is
a peptide or polypeptide chain having at least three amino acid residues and having a sequence that is cleavable by a peptidase or a proteinase; or
a phosphate or phosphate ester that is cleavable by a phosphatase; or
a sulfate or sulfate ester that is cleavable by a sulfatase.

In another embodiment, the compound or salt can be represented by the formula:

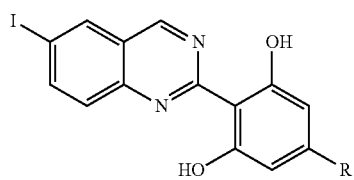
(XXVII)

wherein R is
a peptide or polypeptide chain having at least three amino acid residues and having a sequence that is cleavable by a peptidase or a proteinase; or
a phosphate or phosphate ester that is cleavable by a phosphatase; or
a sulfate or sulfate ester that is cleavable by a sulfatase.

In certain embodiments, a compound of the invention can be hydrolyzed in vivo to yield a compound of Formulae XXVIII-XXXIX:

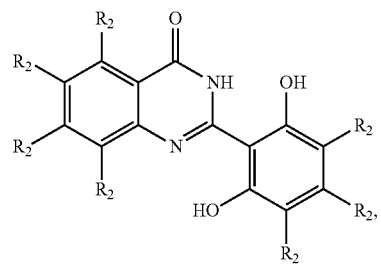
(XXXI)

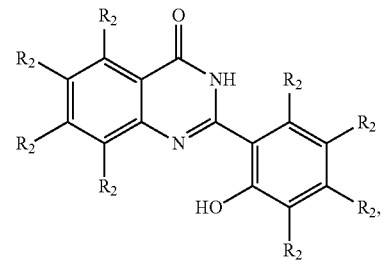
(XXX)

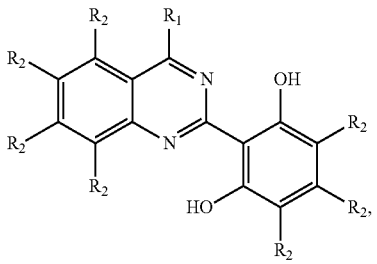
(XXVIII)

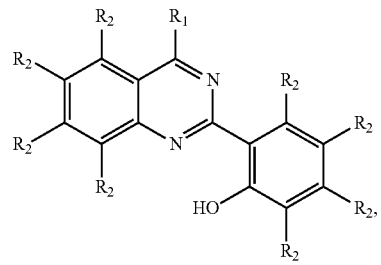
(XXIX)

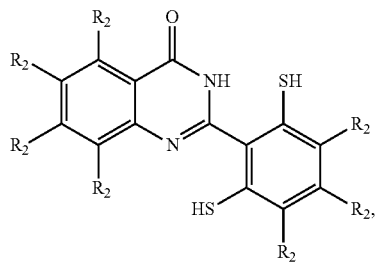
(XXXII)

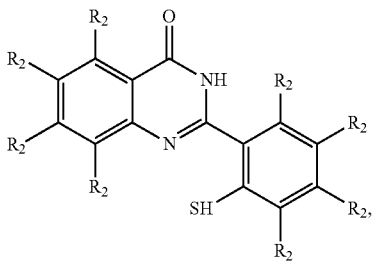
(XXXIII)

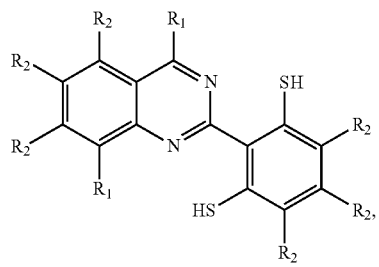
(XXXIV)

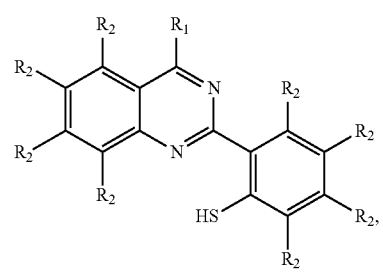
(XXXV)

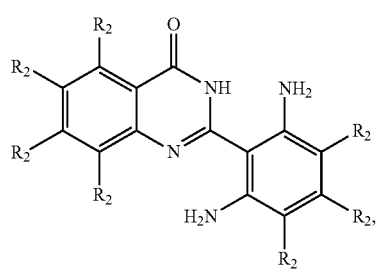
(XXXVI)

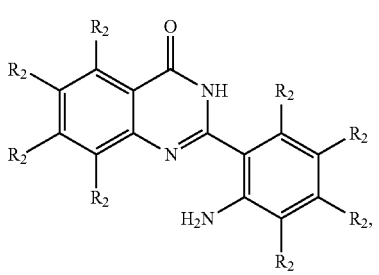
(XXXVII)

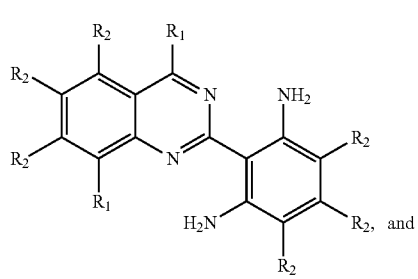
(XXXIII)

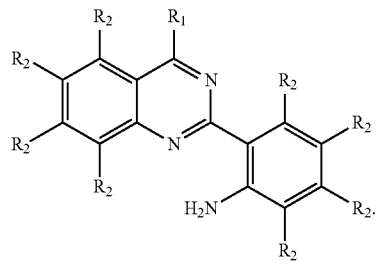
(XXXIX)

In each of Formulae XXVIII-XXXIX, the variable groups $R_1$ and $R_2$ have the meanings of the corresponding variable groups of Formulae I-XXVII.

It will be understood by the skilled artisan that compounds having additional enzyme-cleavable moieties are also within the scope of the invention. For example, in certain embodiments, the invention provides a compound having at least one, two, three, four, five, or more enzyme-cleavable moieties.

The compounds can be prepared according to a variety of methods, some of which are known in the art. For example, certain compounds of the invention can be prepared by reacting a compound of the general formula (a) with a compound of general formula (b) to yield a compound of Formula Ia (see Scheme 1):

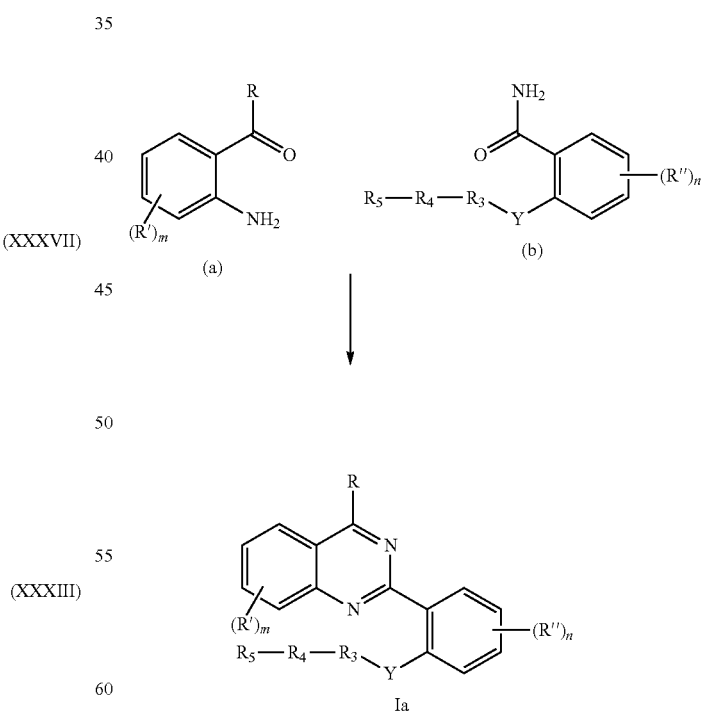

This is an example of the Niementowski quinazoline synthesis. See also U.S. patent Publication US2003/0021791.

In certain embodiments, a compound of the invention can be prepared as shown in Scheme 2.

Scheme 2:

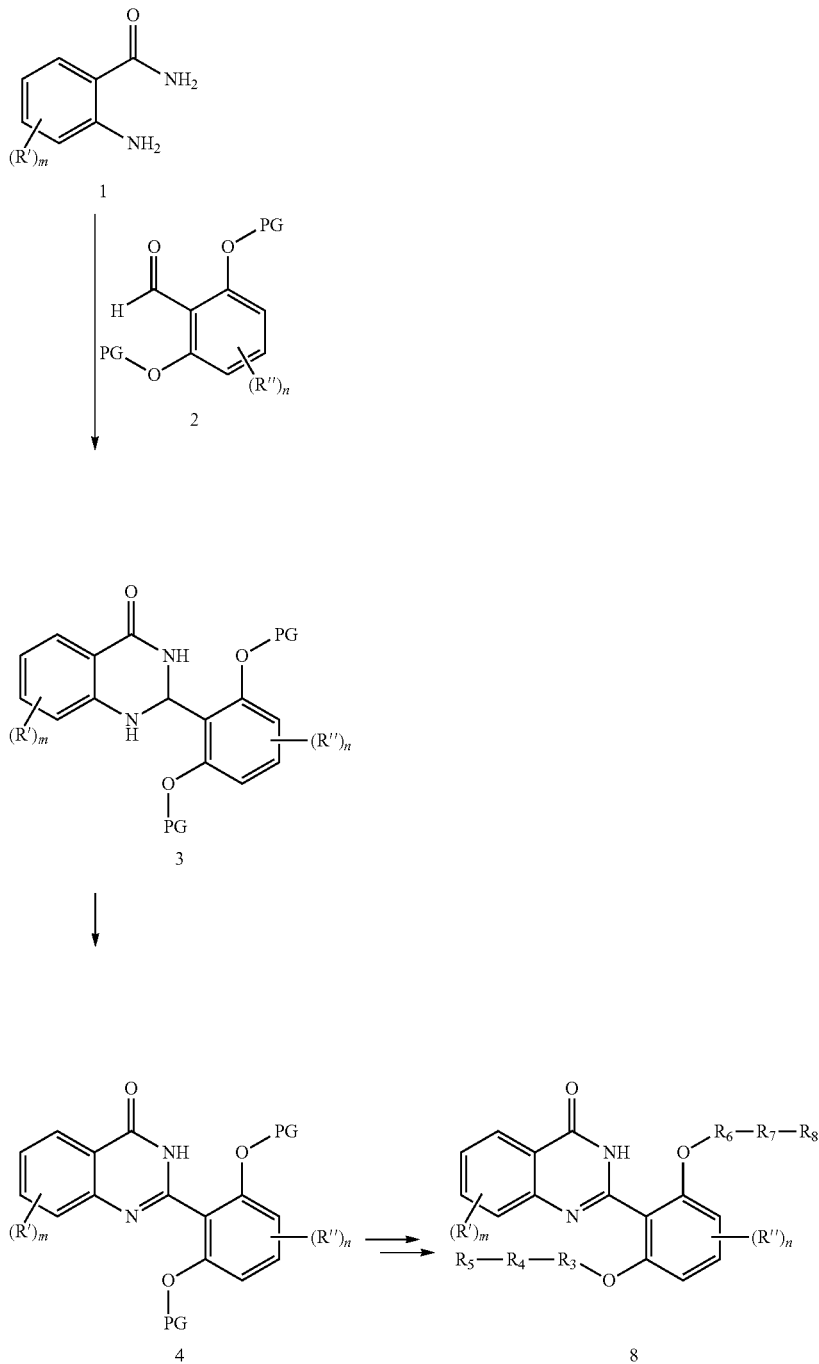

As seen in Scheme 2, an optionally substituted anthranilamide and an optionally substituted salicylaldehyde 2 (in which PG represents a removable protecting group, which may be the same or different for each occurrence) are reacted, e.g., in the presence of an acid such as toluenesulfonic acid to provide a dihydroquinazolinone (3) which can be oxidized (e.g., with dichlorodicyanobenzoquinone (DDQ) to furnish the protected quinazolinone 4. Deprotection of the phenolic hydroxyl group(s) by removal of one or both protecting groups provides a phenolic hydroxyl group(s) which can be elaborated with the enzyme-cleavable moieties $R_3$-$R_8$ (if present) to yield a compound of structure 8.

Similarly, a compound of structure 9 can be prepared as shown in Scheme 3.

Scheme 3.

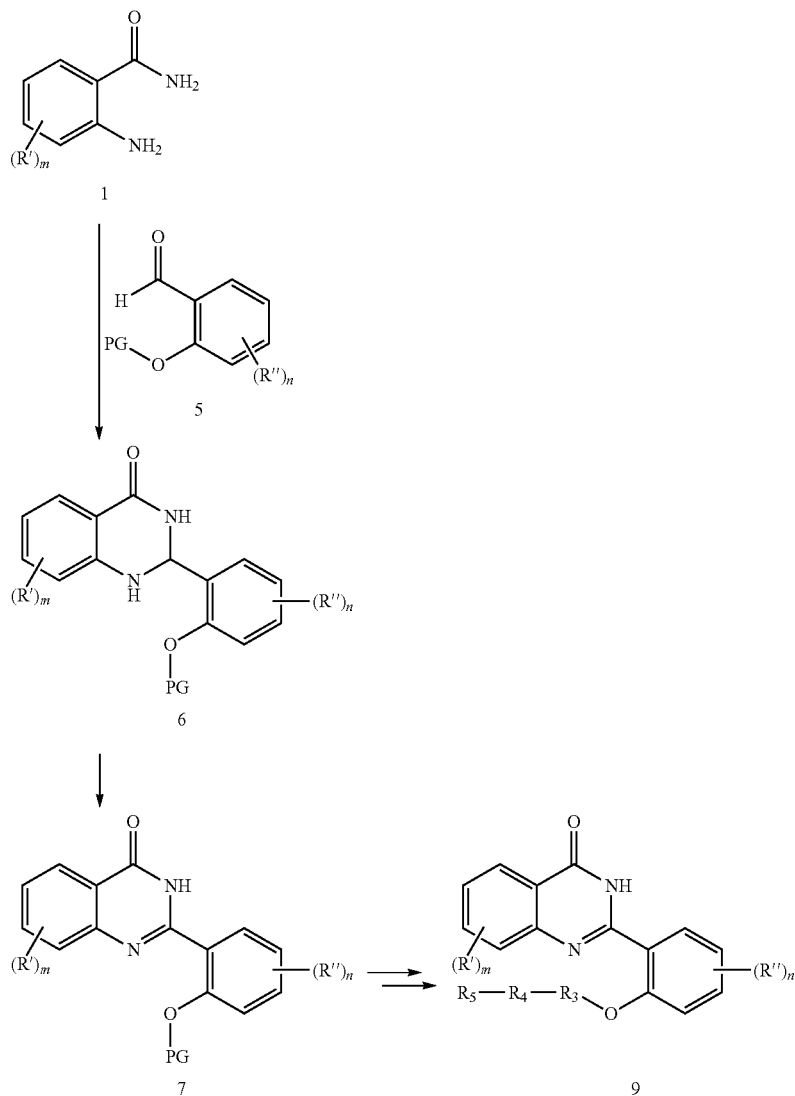

As seen in Scheme 3, an optionally substituted anthranilamide and an optionally substituted salicylaldehyde 5 (in which PG represents a removable protecting group) are reacted, e.g., in the presence of an acid such as toluenesulfonic acid to provide a dihydroquinazolinone (6) which can be oxidized (e.g., with dichlorodicyanobenzoquinone (DDQ) to furnish the protected quinazolinone 7. Deprotection of the phenolic hydroxyl group by removal of the protecting group, followed by elaboration with the enzyme-cleavable moieties $R_3$ and $R_4$ (if present) and $R_5$ yields a compound of structure 9.

In either Scheme 2 or Scheme 3, a protected phenolic hydroxyl group of an intermediate such as compound 4 (Scheme 2) or compound 7 (Scheme 3) can be deprotected to provide a phenolic hydroxyl group capable of further elaboration with the enzyme-cleavable moieties (e.g., $R_3$-$R_8$). For example, in an embodiment in which $R_3$, $R_4$, and $R_5$ are all peptidic substrates for enzymes, a polypeptide reagent of the formula $R_5$—$R_4$—$R_3$—COOH could be coupled to a phenolic hydroxyl group of the quinazolinone 4 or 7 (after removal of a protecting group) under standard coupling conditions. Alternatively, the peptidic moiety $R_3$ (or a protected form thereof) could be coupled to the phenolic hydroxyl group, and the peptidic moieties $R_4$ and $R_5$ could be sequentially coupled to $R_3$ (after deprotection of $R_3$, if necessary), e.g., under standard peptide-coupling conditions, to provide a compound of the invention. Similarly, other enzyme cleavable moieties (such as a phosphate group or sulfate group) can be introduced by reaction of a suitable activated precursor (such as a phosphoryl or sulfonyl chloride) with a phenolic hydroxyl group of an intermediate such as quinazolinone 4 or 7.

It will be appreciated that the protecting groups (e.g., PG in Schemes 2 and 3) can be selected from any of a variety of known protecting groups suitable for selectively protecting phenolic hydroxyl groups (see, e.g., Greene T W et al., *Protective Groups in Organic Synthesis*, 3$^{rd}$ Ed., John Wiley and Sons (1999). Such protective groups can be selected to be stable to certain synthetic conditions while being removable under other conditions. Examples of protective groups include silyl groups (e.g., trimethylsilyl, t-butyldimethylsilyl), esters (e.g., acetate, benzoate), ethers (e.g., methoxymethyl, benzyl), and the like. In the case of intermediates such as compound 4, which have more than one phenolic hydroxyl group, the protective groups can be the same or can be different; the use of selectively (e.g., orthogonally) removable protective groups allows for the selective introduction of the enzyme-cleavable groups $R_3$-$R_8$.

In the compounds of the invention, the radionuclide can be any radioisotope which can produce a photon that can be detected (e.g., in an imaging diagnostic method) and/or a charged energetic particle that delivers a cell-damaging dose of radiation to nearby tissue (for radiotherapeutic applications). Non-limiting examples of radioisotopes include any nuclide suitable for imaging and/or therapy (e.g. Boron-10, Carbon-11, Nitrogen 13, Oxygen-15, Fluorine-18, Phosphorous-32, Phosphorous-33, Technetium-99m, Indium-111, Yttrium-90, Iodine-123, Iodine-124, Iodine-131, Astatine-211, Bismuth-212, etc.). The particular radionuclide can be selected according to the desired application of the compound, e.g., energetic radionuclides capable of cell-damage (e.g., energetic electron (e.g. $^{131}$I) or alpha-particle (e.g. $^{211}$At) emitting radionuclides) will generally be preferred for therapeutic applications, while for diagnostic applications, any suitable detectable radionuclide (e.g., such as a gamma- (e.g. $^{123}$I, $^{99m}$Tc) or positron- (e.g. $^{124}$I, $^{18}$F) emitting radionuclide) can be used.

The language "group which can be cleaved by an enzyme" means a group which can be cleaved under physiological conditions by an enzyme such that the group is removed from the remainder of the molecule. For example, an ester which is susceptible to enzymatic hydrolysis (e.g., hydrolysis promoted by an esterase) is a "group which can be cleaved by an enzyme".

The enzyme cleavable moieties (e.g., $R_3$-$R_8$) can be selected to be cleaved by any enzyme, which preferably is an enzyme found in tumor tissue, and preferably is an extracellular enzyme. Such enzymes include, for example, peptidases, proteinase/proteases, kallikreins, sulfatases, and phosphatases including, but not limited to, prostate specific antigen, matrix metalloproteinases, serine proteinases/proteases, cysteine proteinases/proteases, aspartic proteinases/proteases, threonine proteinase/protease, glutamic acid proteinase/protease, aminopeptidases, carboxypeptidases, dipeptidases, tripeptidases, peptidyle peptidases, guanidinobenzoatase, prostate specific membrane antigen, alkaline phosphatase, prostatic acid phosphatase, and human sulfatase-1 (e.g., extracellular sulfatase-1).

The moieties $R_3$-$R_8$ can be, e.g., an amino acid residue or residues (e.g., from 1-10 amino acid residues) (cleavable by, e.g., peptidases, proteases, and the like); a phosphate group (cleavable by, e.g., phosphateses); a sulfate group (cleavable by, e.g., sulfatases), and the like. In certain embodiments, the compounds of the invention can be targeted to a specific tumor type by appropriate selection of two or more enzyme-cleavable moieties. By appropriate selection of the enzyme-cleavable moieties, the specificity of the compound for a selected tumor type can be increased.

Figure 4:
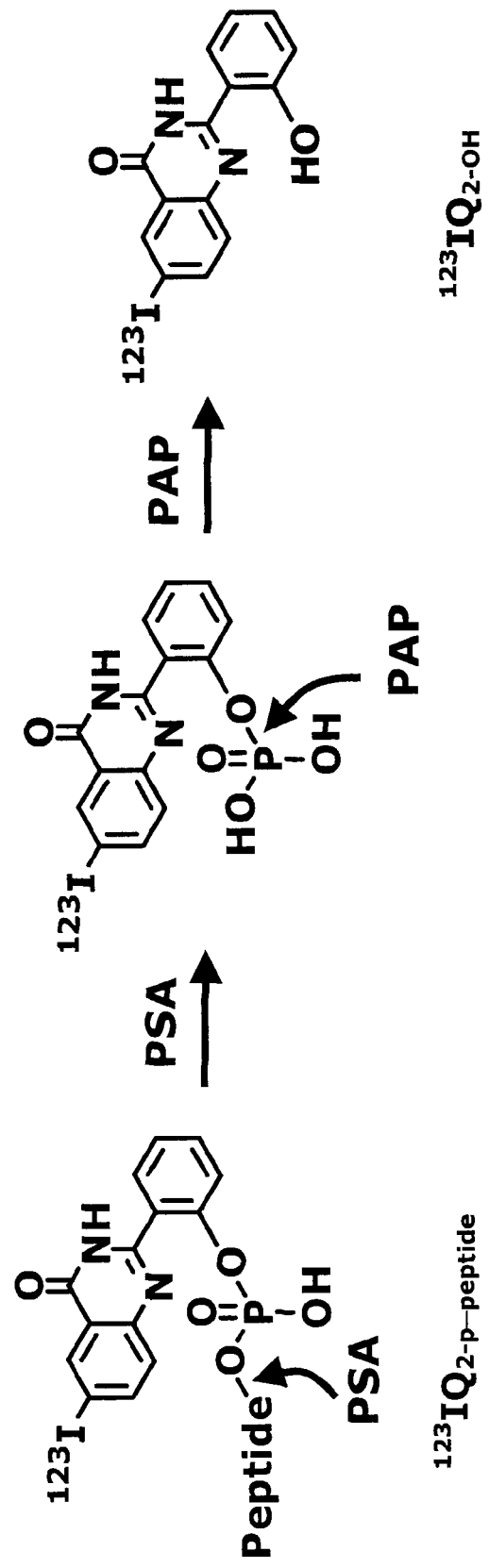
FIG. 4 is a scheme showing one embodiment of a compound of the invention. $^{123}I$=iodine-123; PSA=prostate specific antigen; PAP=prostatic acid phosphatase; Peptide=at least three amino acid residues.
Figure 5:
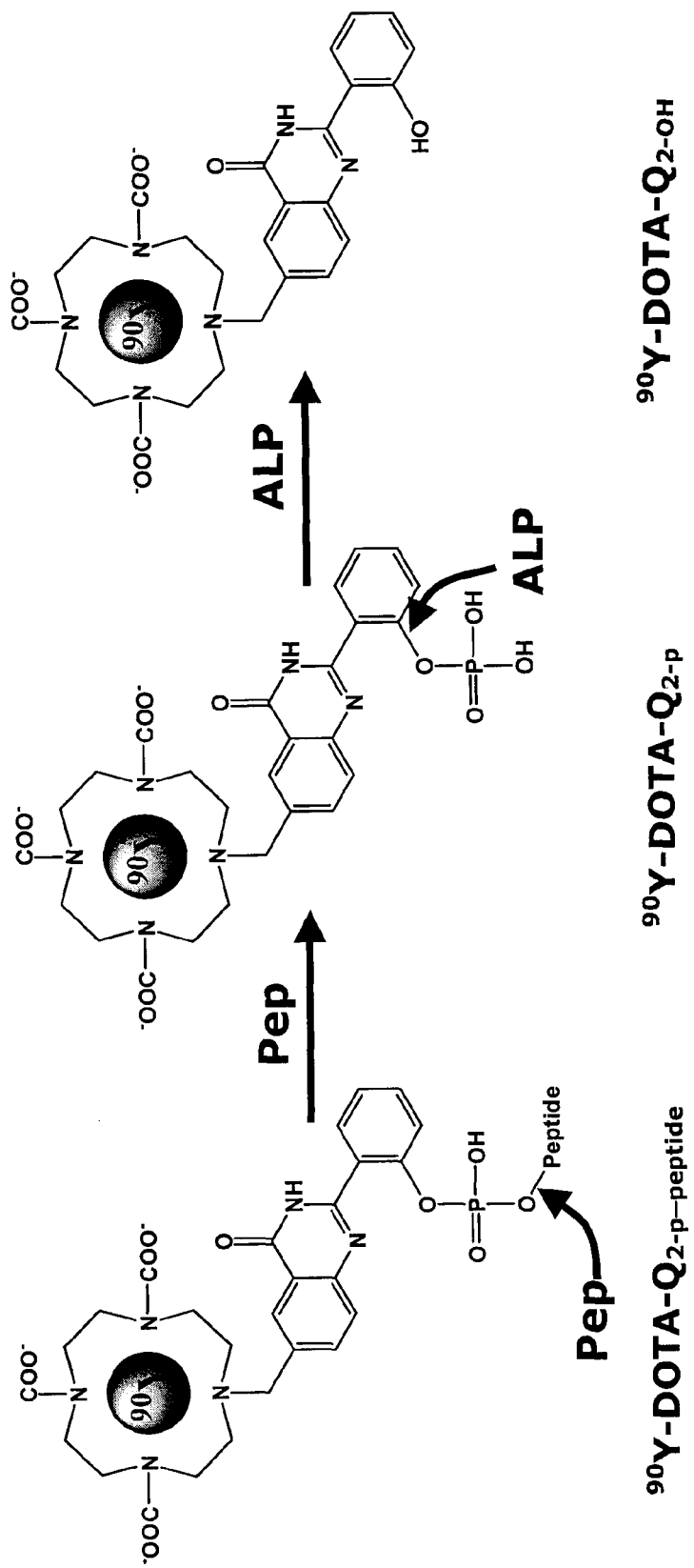
FIG. 5 is a scheme showing one embodiment of a compound of the invention. $^{90}Y$=yttrium-90; DOTA=tetraazacyclododecane tetraacetate; Pep=a peptidase; ALP=alkaline phosphatase; Peptide=at least three amino acid residues.
Figure 6:
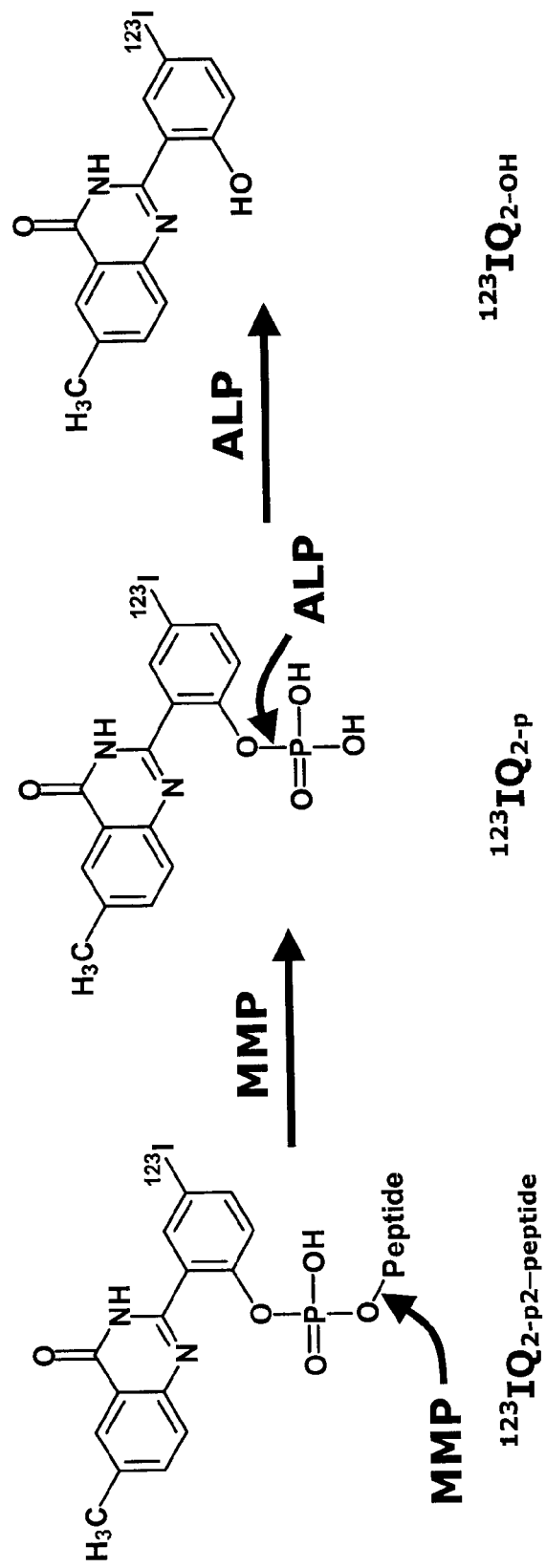
FIG. 6 is a scheme showing one embodiment of a compound of the invention. $^{123}I$=iodine-123; MMP=matrix metalloproteinase; ALP=alkaline phosphatase; Peptide=at least three amino acid residues.
Figure 7:
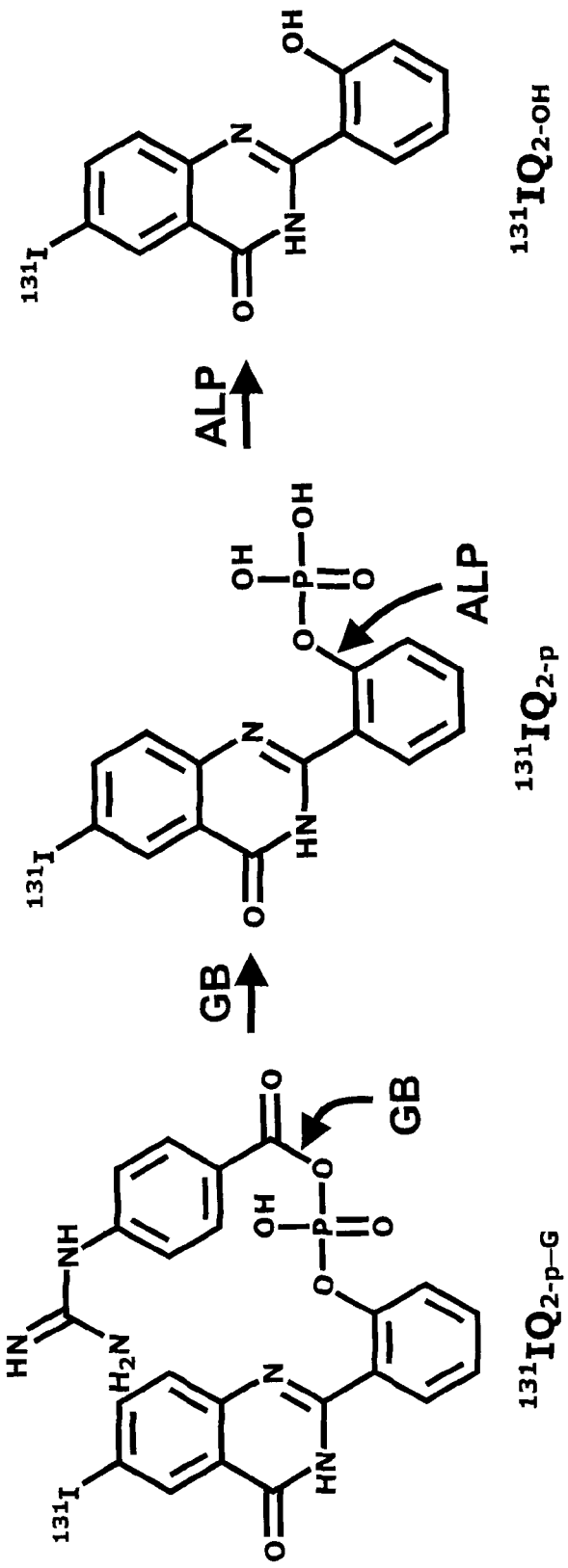
FIG. 7 is a scheme showing one embodiment of a compound of the invention. $^{131}I$=iodine-131; G=guanidinobenzoate; GB=guanidinobenzoatase; ALP=alkaline phosphatase.
Figure 8:
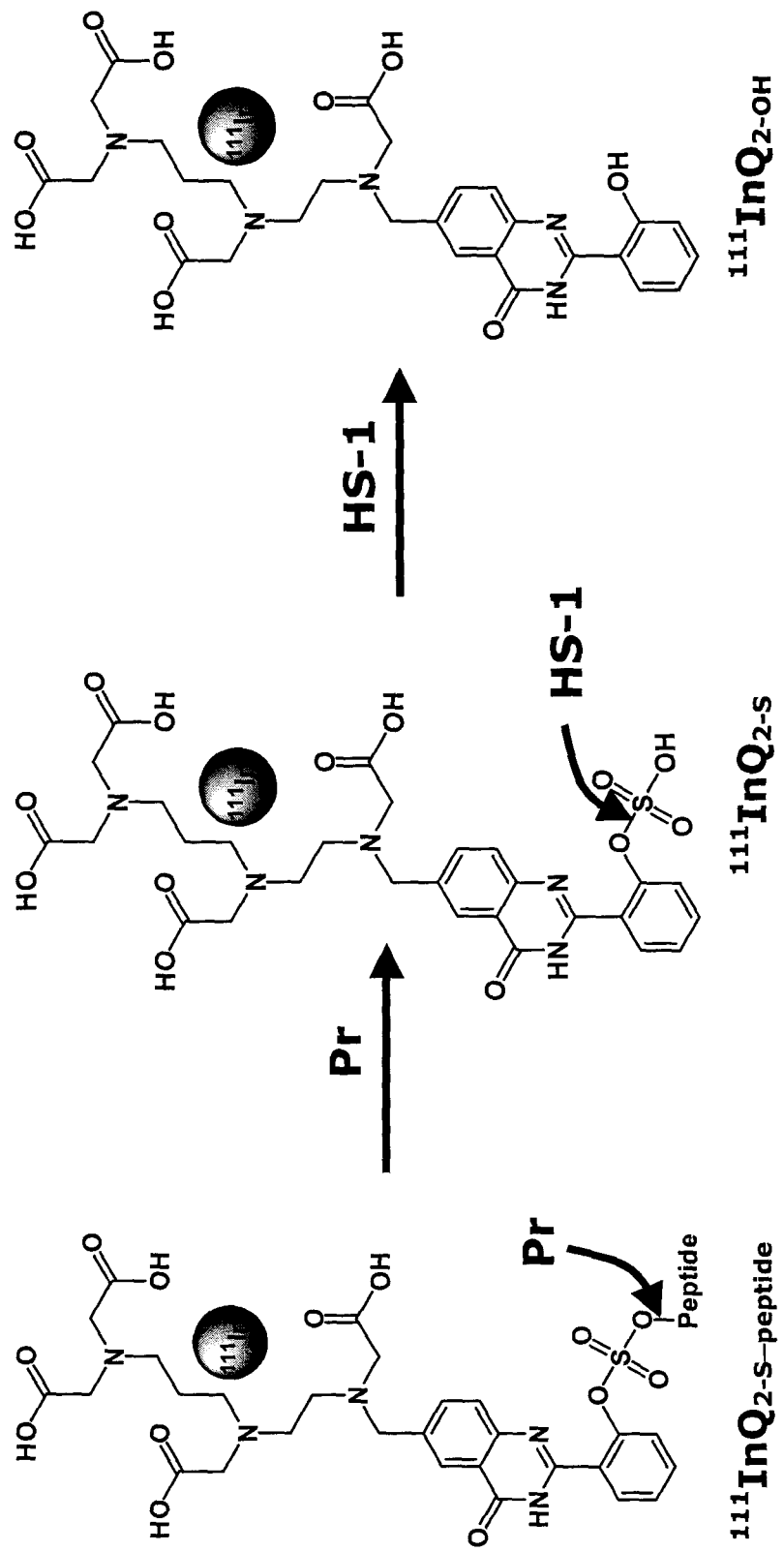
FIG. 8 is a scheme showing one embodiment of a compound of the invention. $^{111}In$=indium-111; DTPA=diethylene triamine pentaacetic acid; Pr=a proteinase; HS-1=human sulfatase-1; Peptide=at least three amino acid residues.
Figure 9:
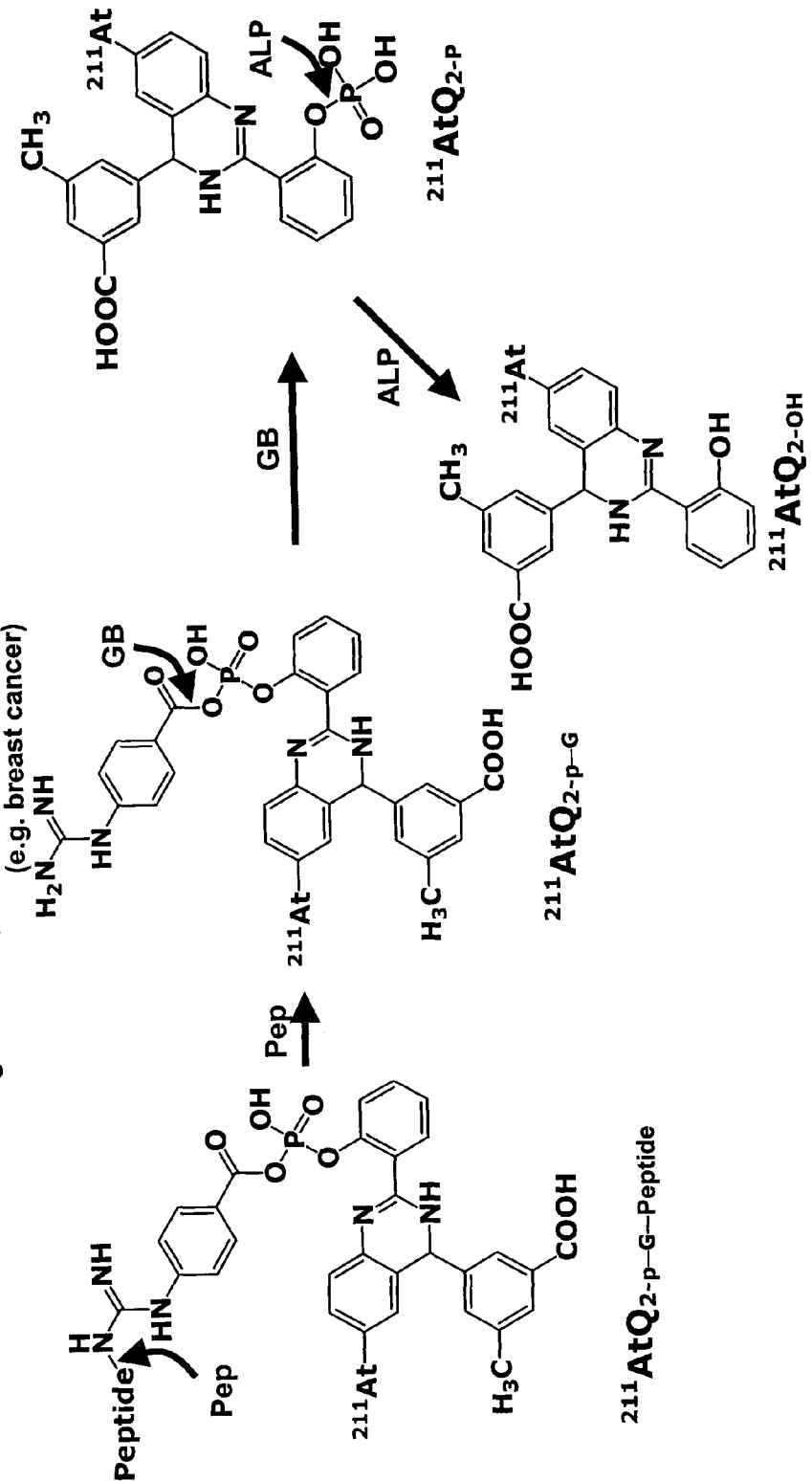
FIG. 9 is a scheme showing one embodiment of a compound of the invention. $^{211}At$=astatine-211; Pep=a peptidase; G=guanidinobenzoate; GB=guanidinobenzoatase; ALP=alkaline phosphatase; Peptide=at least three amino acid residues.

For example, as shown in FIG. 4, a compound of an embodiment of the invention is substituted with a phosphate group and a peptide. The peptidic moiety can be selected to be cleavable by a particular enzyme, e.g., a protease such as PSA, e.g., by selecting peptidic moieties having a cleavage site for which the enzyme is selective. When the compound comes into contact with PSA (e.g., in prostate tumor tissue), the peptidic moiety is cleaved, exposing a phosphate group. A phosphatase such as PAP, which is found in prostate tumor tissue, can cleave the phosphate group, revealing a hydroxyl moiety which can form an intramolecular bond with a nitrogen atom of the quinazoline ring, rendering the compound insoluble and causing the compound to precipitate and become trapped in the prostate tissue.

Suitable enzyme-cleavable prosthetic groups can be selected by a variety of methods. For example, in silico methods can be used to identify water-soluble quinazoline or quinazolinone compounds, e.g., quinazoline or quinazolinone compounds having enzyme-cleavable peptide analogs that are excellent substrates to peptidases/proteinases (e.g. prostate specific antigen—PSA, matrix metalloproteinases—MMP, guanidinobenzoatase—GB, and prostate specific membrane antigen—PSMA) and other hydrolases (e.g. alkaline phosphatase—ALP, prostatic acid phosphatase—PAP, human sulfatase-1—HS) overexpressed extracellularly in solid tumor masses. The hydrolysis of these derivatives occurs sequentially by two or more of these enzymes and leads first to the production of molecules (generally still relatively water-soluble) that are substrates for other enzymes (also overexpressed extracellularly by tumor cells, e.g. alkaline phosphatase—ALP, prostatic acid phosphatase—PAP, or human sulfatase-1—HS). Such hydrolysis leads to the production of water-insoluble RADs. Therefore, the conversion of the water-soluble RAPs to their water-insoluble RAD analogs occurs upon their hydrolysis by one or two or more (consecutively/sequentially) tumor-specific enzyme(s) overexpressed extracellularly by tumor cells (see, e.g., the examples shown herein).

In silico methods can also be used to identify enzymes capable of cleaving a prodrug and appropriate substituents (see, e.g., Pospisil et al., *BMC Bioinformatics* 7:354, 2006, and the "Additional Material" provided therewith) for any of the prodrug compounds of the invention (e.g., a compound of any of Formulae I-III, V-VII, IX-XIV, XVI-XVIII, and XXIV-XXVII). For example, substituents for a compound should be selected so that the pro-drug can be bound by the enzyme and the appropriate enzyme-cleavable moiety is accessible to the catalytic site of the enzyme. Additional guidance in the selection of appropriate compounds can be found, e.g., in Chen et al., *Mol. Cancer. Ther.* 5:3001 (2006); Chen et al., *J. Med. Chem.* 50:663 (2007); and Pospisil et al., *Cancer Res.* 67:2197 (2007).

The compounds of the invention can also be prepared and used as their pharmaceutically acceptable salts. As used herein, the term "pharmaceutically acceptable salt," is a salt formed from an acid and a basic group of one of the compounds of the invention. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

The term "pharmaceutically acceptable salt" also refers to a salt prepared from a compound of the invention having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)-amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)-amine, or tri-(2-hydroxyethyl)amine; N-methyl-D-glucamine; and amino acids such as arginine, lysine, and the like. The term "pharmaceutically acceptable salt" also refers to a salt prepared from a compound disclosed herein, having a basic functional group, such as an amino functional group, and a pharmaceutically acceptable inorganic or organic acid. Suitable acids include, but are not limited to, hydrogen sulfate, citric acid, acetic acid, oxalic acid, hydrochloric acid, hydrogen bromide, hydrogen iodide, nitric acid, phosphoric acid, isonicotinic acid, lactic acid, salicylic acid, tartaric acid, ascorbic acid, succinic acid, maleic acid, besylic acid, fumaric acid, gluconic acid, glucaronic acid, saccharic acid, formic acid, benzoic acid, glutamic acid, methanesulfonic acid, ethanesulfonic acid, benzenesulfonic acid, and p-toluenesulfonic acid.

Methods

The compounds of the invention can be used in a variety of imaging, diagnostic, and therapeutic methods.

For example, in one aspect, the invention provides a method of localizing a substantially water-insoluble drug within the extracellular space of tumor tissue in a subject. The method includes the step of administering a water-soluble prodrug to the subject, wherein the prodrug comprises at least a prosthetic group, wherein the prosthetic group is cleavable by an enzyme, whereby cleavage of the prosthetic group from the prodrug yields the substantially water-insoluble drug, such that the substantially water-insoluble drug is localized within the extracellular space of tumor tissue in a subject.

For example, in one aspect, the invention provides a method of localizing a substantially water-insoluble drug within the extracellular space of tumor tissue in a subject. The method includes the step of administering a water-soluble prodrug to the subject, wherein the prodrug comprises at least a first prosthetic group and a second prosthetic group, wherein the first prosthetic group is cleavable by a first enzyme and the second prosthetic group is cleavable by a second enzyme, whereby cleavage of the first and second prosthetic groups from the prodrug yields the substantially water-insoluble drug, such that the substantially water-insoluble drug is localized within the extracellular space of tumor tissue in a subject.

In certain embodiments, the water-soluble prodrug is a compound of any of Formulae I-III, V-VII, IX-XIV, XVI-XVIII, and XXIV-XXVII herein.

In another aspect, the invention provides a method of localizing a substantially water-insoluble drug within the extracellular space of tumor tissue in a subject, wherein the prodrug comprises at least a first prosthetic group and a second prosthetic group, wherein the first prosthetic group and the second prosthetic groups are both cleavable by a single enzyme, whereby cleavage of the first and second prosthetic groups from the prodrug yields the substantially water-insoluble drug, such that the substantially water-insoluble drug is localized within the extracellular space of tumor tissue in a subject.

In another aspect, the invention provides a method of localizing a substantially water-insoluble drug within the extracellular space of tumor tissue in a subject, wherein the prodrug comprises at least a first prosthetic group and a second prosthetic group, wherein the first prosthetic group is cleavable by a first enzyme and the second prosthetic group is independently cleavable by a second enzyme, whereby cleavage of the first and second prosthetic groups from the prodrug yields the substantially water-insoluble drug, such that the substantially water-insoluble drug is localized within the extracellular space of tumor tissue in a subject.

In still another aspect, the invention provides a method of localizing a substantially water-insoluble drug within the extracellular space of tumor tissue in a subject, wherein the prodrug comprises at least a first prosthetic group and a second prosthetic group, wherein the first prosthetic group is cleavable first by a first enzyme and the second prosthetic group is subsequently cleavable by a second enzyme, whereby cleavage of the first and second prosthetic groups from the prodrug yields the substantially water-insoluble drug, such that the substantially water-insoluble drug is localized within the extracellular space of tumor tissue in a subject.

In yet another aspect, the invention provides a method of localizing a substantially water-insoluble drug within the extracellular space of tumor tissue in a subject, wherein the prodrug comprises at least a first prosthetic group, a second prosthetic group, and a third prosthetic group, wherein the first prosthetic group is cleavable first by a first enzyme, the second prosthetic group is subsequently cleavable by a second enzyme, and the third prosthetic group is subsequently cleaved by a third enzyme, whereby cleavage of the first, second, and third prosthetic groups from the prodrug yields the substantially water-insoluble drug, such that the substantially water-insoluble drug is localized within the extracellular space of tumor tissue in a subject.

In a still further aspect, the invention provides a method of localizing a substantially water-insoluble drug within the extracellular space of tumor tissue in a subject, wherein the prodrug comprises at least a first prosthetic group, a second prosthetic group, a third prosthetic group, and a fourth prosthetic group, wherein the first and fourth prosthetic groups are both cleavable first by a first enzyme, and the second and third prosthetic groups are both subsequently cleavable by a second enzyme, whereby cleavage of the first, second, third, and fourth prosthetic groups from the prodrug yields the substantially water-insoluble drug, such that the substantially water-insoluble drug is localized within the extracellular space of tumor tissue in a subject.

In another aspect, the invention provides a method of localizing a substantially water-insoluble drug within the extracellular space of tumor tissue in a subject, wherein the prodrug comprises at least a first prosthetic group, a second prosthetic group, a third prosthetic group, a fourth prosthetic group, a fifth prosthetic group, and a sixth prosthetic group, wherein the first and sixth prosthetic groups are both cleavable first by a first enzyme, the second and fifth prosthetic groups are both subsequently cleavable by a second enzyme, and the third and fourth prosthetic groups are subsequently cleaved by a third enzyme, whereby cleavage of the first, second, third, fourth, fifth, and sixth prosthetic groups from the prodrug yields the substantially water-insoluble drug, such that the substantially water-insoluble drug is localized within the extracellular space of tumor tissue in a subject.

In certain embodiments of some of the above aspects, at least one of the first and second enzymes is present in the extracellular space of the tumor tissue. In certain embodiments, at least one of the first and second enzymes is produced naturally by cells of the tumor tissue. In certain embodiments, at least one of the first and second enzymes is unique to tumor cells or is produced at concentrations that are higher in tumor cells than in normal tissues. In certain embodiments, at least one of the first and second enzymes is selected from the group consisting of prostate specific antigen, matrix metalloproteinases, guanidinobenzoatase, prostate specific membrane antigen, alkaline phosphatase, prostatic acid phosphatase, and human sulfatase-1.

It will be apparent to the skilled artisan that, in compounds having more than one enzyme-cleavable moieties, the enzyme-cleavable moieties can be the same (in which case the moieties could be cleaved by a single enzyme acting at multiple sites of the compound or by two or more enzymes capable of cleaving that moiety) or can be different (in which case the moieties could be cleaved by a single enzyme capable of cleaving both moieties, or by two or more enzymes).

In another aspect, the invention provides a method of treating a subject suffering from a solid tumor. The method includes the step of administering to the subject an effective amount of a compound of any of Formulae I-III, V-VII, IX-XIV, XVI-XVIII, and XXIV-XXVII, under conditions such that the solid tumor is treated.

Examples of solid tumors include sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

In another aspect, the invention provides a method for diagnosing a solid tumor in a subject. The method includes the steps of administering to the subject an effective amount of a compound of any of Formulae I-III, V-VII, IX-XIV, XVI-XVIII, and XXIV-XXVII, and detecting radiation under conditions such that the patient is diagnosed.

In certain embodiments, at least one of the first and second enzymes is present in the extracellular space of the tumor tissue. In certain embodiments, at least one of the first and second enzymes is produced naturally by cells of the tumor tissue. In certain embodiments, at least one of the first and second enzymes is unique to tumor cells or is produced at concentrations that are higher in tumor cells than in normal tissues. In certain embodiments, at least one of the first and second enzymes is selected from the group consisting of prostate specific antigen, matrix metalloproteinases, guanidinobenzoatase, prostate specific membrane antigen, alkaline phosphatase, prostatic acid phosphatase, and human sulfatase-1. For examples of "two-enzyme" compounds of the invention (compounds having substrates cleavable by two different enzymes), see, e.g., FIG. 4 (a compound with groups cleavable by prostate-specific antigen and prostatic acid phosphatase), FIG. 6 (a compound with groups cleavable by matrix metalloproteinase and alkaline phosphatase), and FIG. 7 (a compound with groups cleavable by guanidinobenzoatase and alkaline phosphatase). For examples of "three-enzyme" compounds of the invention (compounds having substrates cleavable by three different enzymes), see, e.g., FIGS. 9 and 15.

Pretargeting of enzyme or its equivalent species may be achieved by making use of specific antibodies or any such specific receptor-binding ligand to the desired sites in vivo. For example, the ligand may also be a peptide or hormone, with the receptor specific to the peptide or hormone. Alternatively, the enzyme may be produced within the tumor site by the tumor cells themselves or following gene therapy or similar means. Furthermore, the enzyme can optionally be supplied to the tumor site, e.g., by injection of a solution of the enzyme into tumor tissue, to effectively target the radiolabeled compound to the tumor tissue.

In certain embodiments, it may be advantageous to select a compound for therapy based on enzymes expressed or otherwise present at a tumor site. Thus, a prodrug compound can be selected to be efficiently converted to the active RAD by enzymes known or believed to be present at the tumor site. In certain embodiments, a biopsy or other diagnostic test can be preformed on the tumor tissue to determine the enzymes present in the tumor (or the extracellular space thereof), and the prodrug compound to be administered is selected based on the enzymes present. In certain embodiments, suitable enzyme-cleavable moieties are selected, and the prodrug compound is prepared, based on the enzymes associated with the target tumor. See, e.g., Ho et al., *Bioconj. Chem.* 13:357 (2002); Pospisil et al., *BMC Bioinformatics* 7:354 (2006), and the "Additional Information" provided therein; Chen et al., *Mol. Cancer. Ther.* 5:3001 (2006); Chen et al., *J. Med. Chem.* 50:663 (2007); and Pospisil et al., *Cancer Res.* 67:2197 (2007).

Pharmaceutical Formulations

The phrase "pharmaceutically acceptable carrier" is art recognized and includes a pharmaceutically acceptable material, composition or vehicle, suitable for administering compounds of the present invention to a subject, e.g., to a mammal. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that enables external imaging (SPECT/PET) or produces a therapeutic effect. Generally, out of one hundred percent, this amount will range from about 0.000006 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue.

The preparations of the present invention may be given orally, parenterally, topically, rectally, or vaginally. They are of course given by forms suitable for each administration route. For example, they are administered in tablets or capsule form, by injection, inhalation, eye lotion, ointment, suppository, etc. administration by injection, infusion or inhalation; topical by lotion or ointment; vaginal; and rectal by suppositories. Intravenous injection is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the decay characteristics of the radionuclide and its physical half-life of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic or diagnostic effect. Such an effective dose will generally depend upon the factors described above. Generally, intravenous, intralymphatic, and subcutaneous doses of the compounds of this invention for a patient, when used for the indicated imaging effects, will range from about 5 to about 30 mCi, depending on the radioisotope employed. An effective therapeutic amount will typically range about 10 mCi to about 2 Ci. An effective amount is the amount that treats or images a solid tumor.

If desired, the effective daily or weekly dose of the active compound may be administered as two, three, four, five, six or more sub-doses administered separately at appropriate intervals throughout the day or other time period, optionally, in unit dosage forms.

While it is possible for a compound of the present invention to be administered alone, it is preferable to administer the compound as a pharmaceutical composition. Moreover, the pharmaceutical compositions described herein may be administered with one or more other active ingredients that would aid in treating a subject having a solid tumor. In a related embodiment, the pharmaceutical compositions of the invention may be formulated to contain one or more additional active ingredients that would aid in treating a subject having a solid tumor, e.g., conventional anticancer compounds and the like.

The disclosures of each and every patent, patent application and publication cited herein are hereby incorporated herein by reference in their entirety.

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

What is claimed is:

1. A compound represented by the formula

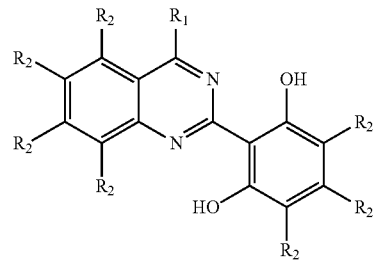

(XXVIII)

in which $R_1$ is H, COOH, amino, mono- or di($C_1$-$C_6$alkyl)amino, $C_1$-$C_8$alkyl, $C_2$-$C_8$alkenyl, $C_3$-$C_8$cycloalkyl, aryl, halogen, $C_1$-$C_8$alkoxy, nitro, or cyano; or $R_1$ is a radionuclide or a moiety complexed with a radionuclide; and $R_2$ is, independently for each occurrence, H, hydroxy, COOH, amino, mono- or di($C_1$-$C_6$alkyl)amino, $C_1$-$C_8$alkyl, $C_2$-$C_8$alkenyl, $C_2$-$C_8$alkynyl, $C_3$-$C_8$cycloalkyl, aryl, halogen, $C_1$-$C_8$alkoxy, nitro, cyano, or a radionuclide or a moiety containing, or capable of complexing with, a radionuclide;

or a pharmaceutically acceptable salt thereof.

wherein the radionuclide is $^{10}$B, $^{11}$C, $^{13}$N, $^{15}$O, $^{32}$P, $^{33}$P, $^{212}$Bi, $^{123}$I, $^{131}$I, $^{111}$In, $^{99m}$Tc, $^{124}$I, $^{18}$F, $^{90}$Y, $^{211}$At, or $^{213}$Bi, and wherein at least one occurrence of $R_1$ or $R_2$ is a radionuclide or moiety complexed with a radionuclide.

2. The compound of clam 1 of formula

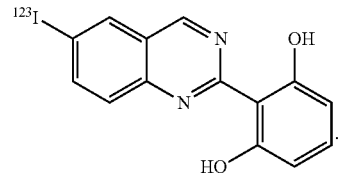 [SMILES: Oc1cccc(O)c1-c1ncc2cc([123I])ccc2n1]

3. A pharmaceutical composition comprising a compound claim 1 together with a pharmaceutically-acceptable carrier.

4. A pharmaceutical composition comprising a compound of claim 2 together with a pharmaceutically-acceptable carrier.

* * * * *